(12) United States Patent
Yokoyama et al.

(10) Patent No.: US 9,196,839 B2
(45) Date of Patent: Nov. 24, 2015

(54) COMPOUND HAVING TRIPHENYLAMINE STRUCTURE, AND ORGANIC ELECTROLUMINESCENT DEVICE

(75) Inventors: Norimasa Yokoyama, Tokyo (JP); Makoto Nagaoka, Tsukuba (JP); Kouki Kase, Tsukuba (JP); Shingo Ozawa, Tsukuba (JP); Shigeru Kusano, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 446 days.

(21) Appl. No.: 13/574,923

(22) PCT Filed: Jan. 25, 2011

(86) PCT No.: PCT/JP2011/000376
§ 371 (c)(1),
(2), (4) Date: Jul. 24, 2012

(87) PCT Pub. No.: WO2011/093056
PCT Pub. Date: Aug. 4, 2011

(65) Prior Publication Data
US 2012/0292609 A1    Nov. 22, 2012

(30) Foreign Application Priority Data

Jan. 26, 2010 (JP) ................. 2010-014265

(51) Int. Cl.
| | |
|---|---|
| *H01L 51/50* | (2006.01) |
| *H01L 51/00* | (2006.01) |
| *C07C 211/54* | (2006.01) |
| *C07C 211/56* | (2006.01) |
| *C07D 209/86* | (2006.01) |
| *C09K 11/06* | (2006.01) |

(52) U.S. Cl.
CPC .......... *H01L 51/0059* (2013.01); *C07C 211/54* (2013.01); *C07C 211/56* (2013.01); *C07D 209/86* (2013.01); *C09K 11/06* (2013.01);
(Continued)

(58) Field of Classification Search
None
See application file for complete search history.

(56) References Cited

U.S. PATENT DOCUMENTS

| | | |
|---|---|---|
| 5,639,914 A | 6/1997 | Tomiyama et al. |
| 5,707,747 A | 1/1998 | Tomiyama et al. |

(Continued)

FOREIGN PATENT DOCUMENTS

| | | |
|---|---|---|
| EP | 2299509 A1 | 3/2011 |
| JP | 07-126225 A | 5/1995 |

(Continued)

OTHER PUBLICATIONS

Murase et al., Analysis of Dark Spots Growing in Organic EL Devices by Time-of-Flight Secondary Ion Mass Spectrometry, 2001, Anal. Chem., vol. 73, pp. 2245-2253.*

(Continued)

*Primary Examiner* — Gregory Clark
(74) *Attorney, Agent, or Firm* — Locke Lord LLP; James E. Armstrong, IV; Nicholas J. DiCeglie, Jr.

(57) ABSTRACT

There is provided an organic compound of excellent characteristics that exhibits excellent hole-injecting/transporting performance and has an electron blocking ability and a highly stable thin-film state with excellent heat resistance. The compound of the present invention is an arylamine compound having a triphenylamine structure. The arylamine compound is used as a constituent material of at least one organic layer in an organic electroluminescent device that includes a pair of electrodes, and one or more organic layers sandwiched between the pair of electrodes.

4 Claims, 8 Drawing Sheets

(52) U.S. Cl.
CPC ......... *C07B2200/05* (2013.01); *C07C 2103/18* (2013.01); *C09K 2211/1014* (2013.01); *H01L 51/5048* (2013.01); *H01L 51/5088* (2013.01); *H01L 51/5096* (2013.01)

(56) References Cited

U.S. PATENT DOCUMENTS

| | | | |
|---|---|---|---|
| 7,321,066 B2 * | 1/2008 | Kawamura et al. | 564/385 |
| 2004/0263067 A1 | 12/2004 | Saitoh et al. | |
| 2005/0064237 A1 | 3/2005 | Kato et al. | |
| 2008/0191614 A1 * | 8/2008 | Kim et al. | 313/504 |
| 2008/0286605 A1 | 11/2008 | Takeda | |

FOREIGN PATENT DOCUMENTS

| | | |
|---|---|---|
| JP | 07-126226 A | 5/1995 |
| JP | 3220950 B2 | 10/2001 |
| JP | 2005-044791 A | 2/2005 |
| JP | 2005-048004 A | 2/2005 |
| JP | 2008-532998 A | 8/2008 |
| JP | 2009-231516 A | 10/2009 |
| WO | WO-2006/095951 A1 | 9/2006 |
| WO | WO-2006/121237 A1 | 11/2006 |
| WO | WO-2007/105917 A1 | 9/2007 |
| WO | WO-2008/117889 A1 | 10/2008 |

OTHER PUBLICATIONS

Office Action issued in corresponding Taiwanese Patent Application No. TW 100102890, dated Oct. 7, 2014.
Office Action mailed Aug. 2, 2013, issued for the Chinese patent application No. 201180007234.3 and Japanese translation thereof.
Supplementary European Search Report dated Oct. 1, 2013, issued for the European patent application No. 11736773.0.
International Search Report dated May 10, 2011, issued for PCT/JP2011/000376.

* cited by examiner

COMPOUND HAVING TRIPHENYLAMINE STRUCTURE, AND ORGANIC ELECTROLUMINESCENT DEVICE

TECHNICAL FIELD

The present invention relates to compounds suited for an organic electroluminescent device (hereinafter, simply referred to as "organic EL device"), a preferred self light-emitting device for various display devices, and to the device. Specifically, the invention relates to compounds having a triphenylamine structure, and to organic EL devices that use the compounds.

BACKGROUND ART

The organic EL device is a self-emitting device, and has been actively studied for their brighter, superior viewability and ability to display clearer images compared with the liquid crystal device.

In 1987, C. W. Tang et al. at Eastman Kodak developed a laminated structure device using materials assigned with different roles, realizing practical applications of an organic EL device with organic materials. These researchers laminated tris(8-hydroxyquinoline)aluminum (an electron-transporting phosphor; hereinafter, simply $Alq_3$), and a hole-transporting aromatic amine compound, and injected the both charges into the phosphor layer to cause emission in order to obtain a high luminance of 1,000 $cd/m^2$ or more at a voltage of 10 V or less (see, for example, Non-Patent Document 1).

To date, various improvements have been made for practical applications of the organic EL device. In order to realize high efficiency and durability, various roles are further subdivided to provide an electroluminescent device that includes an anode, a hole injection layer, a hole transport layer, a light emitting layer, an electron transport layer, an electron injection layer, and a cathode successively formed on a substrate (see, for example, Non-Patent Document 2).

Further, there have been attempts to use triplet excitons for further improvements of luminous efficiency, and use of phosphorescent materials has been investigated (see, for example, Non-Patent Document 3).

The light emitting layer can also be fabricated by doping a charge-transporting compound, generally called a host material, with a phosphor or a phosphorescent material. As described in the foregoing lecture preprints, selection of organic materials in an organic EL device greatly influences various device characteristics, including efficiency and durability.

In an organic EL device, the charges injected from the both electrodes recombine at the light emitting layer to cause emission. Here, it is important how efficiently the hole and electron charges are transferred to the light emitting layer. The probability of hole-electron recombination can be improved by improving the hole injectability and the electron blocking performance of blocking the injected electrons from the cathode, and high luminous efficiency can be obtained by confining the excitons generated in the light emitting layer. The role of the hole transport material is therefore important, and there is a need for a hole transport material that has high hole injectability, high hole mobility, high electron blocking performance, and high electron durability.

There is also a need for a hole transport material that is stable as a thin film, and has high heat resistance.

Various aromatic amine derivatives are known as the hole transport materials used for the organic EL device (see, for example, Patent Documents 1 and 2). These compounds include a compound known to have an excellent hole mobility of $10^{-3}$ $cm^2/Vs$ or higher. However, for higher efficiency, a material with higher electron blocking performance, a more stable thin-film state, and higher heat resistance is needed.

There is a report of a high-efficient organic EL device obtained by using a deuterium atom-substituted light emitting layer material (see, for example, Patent Documents 3 and 4).

This is an application of the principle that the luminous efficiency increases by facilitating the formation of excitons when substituted with deuterium atom. While this is true for the material of the light emitting layer, the technique cannot be applied to the material of the hole transport layer. In fact, there is no known example of an application to the material of the hole transport layer.

CITATION LIST

Patent Documents

Patent Document 1: JP-A-8-048656
Patent Document 2: Japanese Patent Number 3194657
Patent Document 3: JP-T-2008-532998 (the term "JP-T" as used herein means a published Japanese translation of a PCT patent application)
Patent Document 4: JP-A-2009-231516
Patent Document 5: JP-A-7-126615

Non-Patent Documents

Non-Patent Document 1: Appl. Phys. Lett., 51, 913 (1987)
Non-Patent Document 2: The Japan Society of Applied Physics, 9th lecture preprints, pp. 55 to 61 (2001)
Non-Patent Document 3: The Japan Society of Applied Physics, 9th lecture preprints, pp. 23 to 31 (2001)

SUMMARY OF THE INVENTION

Problems that the Invention is to Solve

It is an object of the present invention to provide an organic compound of excellent characteristics that exhibits excellent hole-injecting/transporting performance with an electron blocking ability, and that has high stability in the thin-film state and excellent heat resistance, the organic compound being provided as a material of a high-efficient, high-durable organic EL device. The invention also provides a high-efficient, high-durable organic EL device, using the compound.

Some of the physical properties of the organic compound provided by the present invention include (1) good hole injection characteristics, (2) high hole mobility, (3) excellent electron blocking ability, (4) stability in the thin-film state, and (5) excellent heat resistance. Some of the physical properties of the organic EL device to be provided by the present invention include (1) high luminous efficiency and high power efficiency, (2) low turn on voltage, and (3) low actual driving voltage.

Means for Solving the Problems

In order to achieve the foregoing objects, the present inventors focused on the high hole-injecting/transporting performance of a triphenylamine structure, and produced various test organic EL devices by designing and chemically synthesizing compounds having a triphenylamine structure, in anticipation that the triphenylamine structure, upon substitution with a deuterium atom, would effectively improve heat resistance and thin film stability. The present invention was completed after thorough evaluations of the device characteristics.

Specifically, the present invention is an arylamine compound of the following general formula (1) having two triphenylamine structures connected to each other by a single bond or by a divalent group that does not contain a heteroatom.

[Chemical Formula 1] (1)

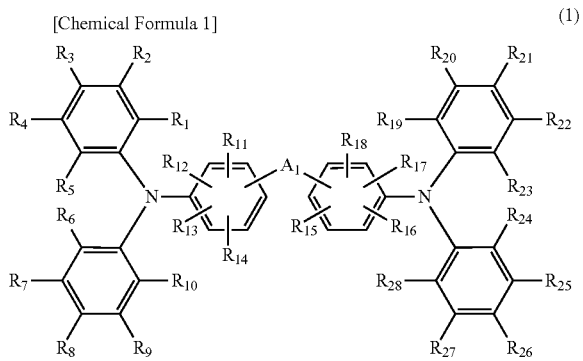

(In the formula, R1 to R28 may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other to form a ring. At least one of R1 to R28 is a deuterium atom, or a substituent that contains a deuterium atom. A1 represents the divalent group of the structural formulae (B) to (F) below, or a single bond.)

[Chemical Formula 2] (B)

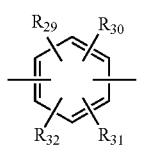

(In the formula, R29 to R32 may be the same or different, and represent a hydrogen atom or a deuterium atom.)

[Chemical Formula 3] (C)

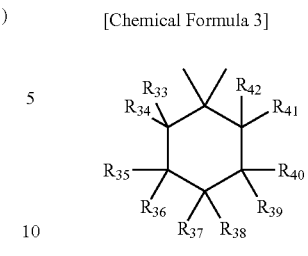

(In the formula, R33 to R42 may be the same or different, and represent a hydrogen atom or a deuterium atom.)

[Chemical Formula 4] (D)

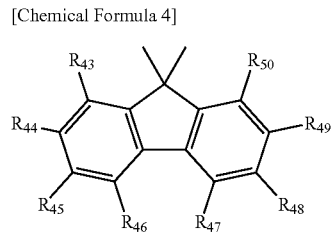

(In the formula, R43 to R50 may be the same or different, and represent a hydrogen atom or a deuterium atom.)

[Chemical Formula 5] (E)

—$CH_2$—

[Chemical Formula 6] (F)

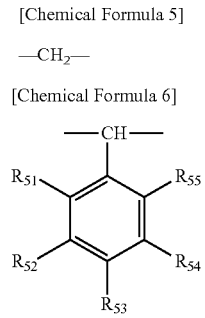

(In the formula, R51 to R55 may be the same or different, and represent a hydrogen atom or a deuterium atom.)

Further, the present invention is an arylamine compound of the following general formula (2) having four triphenylamine structures connected by a single bond or by a divalent group that does not contain a heteroatom.

[Chemical Formula 7] (2)

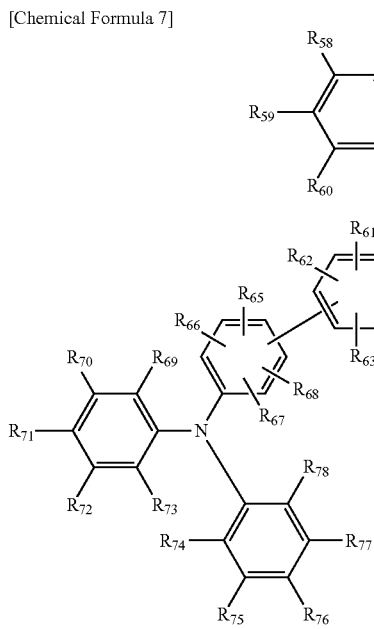
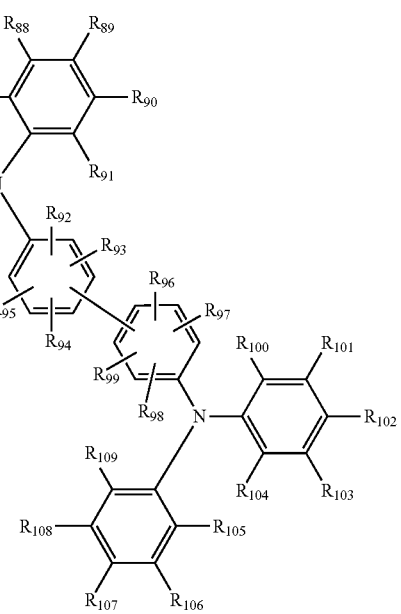

(In the formula, R56 to R109 may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other to form a ring. At least one of R56 to R109 is a deuterium atom, or a substituent that contains a deuterium atom. A2 represents the divalent group of the structural formulae (B) to (F) below, or a single bond.)

[Chemical Formula 8]

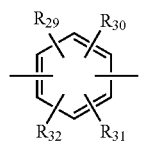

(B)

(In the formula, R29 to R32 may be the same or different, and represent a hydrogen atom or a deuterium atom.)

[Chemical Formula 9]

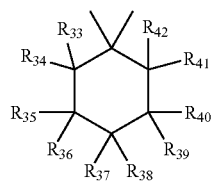

(C)

(In the formula, R33 to R42 may be the same or different, and represent a hydrogen atom or a deuterium atom.)

[Chemical Formula 10]

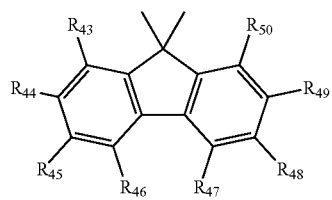

(D)

(In the formula, R43 to R50 may be the same or different, and represent a hydrogen atom or a deuterium atom.)

[Chemical Formula 11]

—CH$_2$— (E)

[Chemical Formula 12]

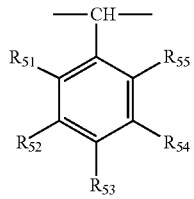

(F)

(In the formula, R51 to R55 may be the same or different, and represent a hydrogen atom or a deuterium atom.)

Further, the present invention is an organic electroluminescent device that includes a pair of electrodes, and one or more organic layers sandwiched between the pair of electrodes, wherein the arylamine compound represented by the general formula (1) or (2) is used as a constituent material of at least one organic layer.

Specific examples of the "linear or branched alkyl of 1 to 6 carbon atoms", "cycloalkyl of 5 to 10 carbon atoms", or "linear or branched alkenyl of 2 to 6 carbon atoms" in the "linear or branched alkyl of 1 to 6 carbon atoms that may have a substituent", "cycloalkyl of 5 to 10 carbon atoms that may have a substituent", or "linear or branched alkenyl of 2 to 6 carbon atoms that may have a substituent" represented by R1 to R28 or R56 to R109 in the general formulae (1) and (2) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These substituents may bind to each other to form a ring.

Specific examples of the substituent in the "linear or branched alkyl of 1 to 6 carbon atoms having a substituent", "cycloalkyl of 5 to 10 carbon atoms having a substituent", or "linear or branched alkenyl of 2 to 6 carbon atoms having a substituent" represented by R1 to R28 or R56 to R109 in the general formulae (1) and (2) include a deuterium atom, trifluoromethyl, cyano, nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxys of 1 to 6 carbon atoms such as methoxy, ethoxy, and propyloxy; alkenyls such as allyl; aralkyls such as benzyl, naphthylmethyl, and phenethyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups, such as diphenylamino and dinaphthylamino, substituted with aromatic hydrocarbon groups or condensed polycyclic aromatic groups; diaralkylamino groups such as dibenzylamino and diphenethylamino; disubstituted amino groups, such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with other substituents.

Specific examples of the "linear or branched alkyloxy of 1 to 6 carbon atoms" or "cycloalkyloxy of 5 to 10 carbon atoms" in the "linear or branched alkyloxy of 1 to 6 carbon atoms that may have a substituent" or "cycloalkyloxy of 5 to 10 carbon atoms that may have a substituent" represented by R1 to R28 or R56 to R109 in the general formulae (1) and (2) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These substituents may bind to each other to form a ring.

Specific examples of the substituent in the "linear or branched alkyloxy of 1 to 6 carbon atoms having a substituent" or "cycloalkyloxy of 5 to 10 carbon atoms having a substituent" represented by R1 to R28 or R56 to R109 in the general formulae (1) and (2) include a deuterium atom, trifluoromethyl, cyano, nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkoxys of 1 to 6 carbon atoms such as methoxy, ethoxy, and propyloxy; alkenyls such as allyl; aralkyls such as benzyl, naphthylmethyl, and phenethyl; aryloxys such as phenoxy and tolyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups, such as diphenylamino and dinaphthylamino, substituted with aromatic hydrocarbon groups or condensed polycyclic aromatic groups; diaralkylamino groups such as dibenzylamino and diphenethylamino; disubstituted amino groups, such as dipyridylamino and dithienylamino group, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with other substituents.

Specific examples of the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by R1 to R28 or R56 to R109 in the general formulae (1) and (2) include phenyl, biphenylyl, terphenylyl, naphthyl, anthryl, phenanthryl, fluorenyl, indenyl, pyrenyl, perylenyl, fluoranthenyl, triphenylenyl, pyridyl, furanyl, pyranyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl. These substituents may bind to each other to form a ring.

Specific examples of the substituent in the "substituted aromatic hydrocarbon group", "substituted aromatic heterocyclic group", or "substituted condensed polycyclic aromatic group" represented by R1 to R28 or R56 to R109 in the general formulae (1) and (2) include a deuterium atom, cyano, trifluoromethyl, nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; cycloalkyls of 5 to 10 carbon atoms such as cyclopentyl and cyclohexyl; linear or branched alkenyls of 2 to 6 carbon atoms such as vinyl, allyl, 2-butenyl, and 1-hexenyl; linear or branched alkyloxys of 1 to 6 carbon atoms such as methoxy, ethoxy, and propyloxy; cycloalkyloxys of 5 to 10 carbon atoms such as cyclopentyloxy, and cyclohexyloxy; aralkyls such as benzyl, naphthylmethyl, and phenethyl; aryloxys such as phenoxy, tolyloxy, biphenylyloxy, terphenylyloxy, naphthyloxy, anthryloxy, phenanthryloxy, fluorenyloxy, indenyloxy, pyrenyloxy, and perylenyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl, and benzoyl; dialkylamino groups such as dimethylamino and diethylamino; disubstituted amino groups, such as diphenylamino and dinaphthylamino, substituted with aromatic hydrocarbon groups or condensed polycyclic aromatic groups; diaralkylamino groups such as dibenzylamino and diphenethylamino; disubstituted amino groups, such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with other substituents.

Specific examples of the "aryloxy" in the "substituted or unsubstituted aryloxy" represented by R1 to R28 or R56 to R109 in the general formulae (1) and (2) include phenoxy, tolyloxy, biphenylyloxy, terphenylyloxy, naphthyloxy, anthryloxy, phenanthryloxy, fluorenyloxy, indenyloxy, pyrenyloxy, and perylenyloxy. These substituents may bind to each other to form a ring.

Specific examples of the substituent in the "substituted aryloxy" represented by R1 to R28 or R56 to R109 in the general formulae (1) and (2) include a deuterium atom, cyano, trifluoromethyl, nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; cycloalkyls of 5 to 10 carbon atoms such as cyclopentyl, and cyclohexyl; linear or branched alkenyls of 2 to 6 carbon atoms such as vinyl, allyl, 2-butenyl, and 1-hexenyl; linear or branched alkyloxys of 1 to 6 carbon atoms such as methoxy, ethoxy, and propyloxy; cycloalkyloxys of 5 to 10 carbon atoms such as cyclopentyloxy, and cyclohexyloxy; aralkyls such as benzyl, naphthylmethyl, and phenethyl; aryloxys such as phenoxy, tolyloxy, biphenylyloxy, terphenylyloxy, naphthyloxy, anthryloxy, phenanthryloxy, fluorenyloxy, indenyloxy, pyrenyloxy, and perylenyloxy; arylalkoxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, furanyl, pyranyl, thienyl, furyl, pyrrolyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups, such as diphenylamino and dinaphthylamino, substituted with aromatic hydrocarbon groups or condensed polycyclic aromatic groups; diaralkylamino groups such as dibenzylamino and diphenethylamino; disubstituted amino groups, such as dipyridylamino and dithienylamino, substituted with aromatic heterocyclic groups; dialkenylamino groups such as dialkylamino; and disubstituted amino group substituted with a substituent selected from alkyl, an aromatic hydrocarbon group, a condensed polycyclic aromatic group, aralkyl, an aromatic heterocyclic group, and alkenyl. These substituents may be further substituted with other substituents.

Among the arylamine compounds of the general formula (1), the arylamine compounds of the following general formula (1') or (1") are preferably used for an organic EL device.

[Chemical Formula 13]

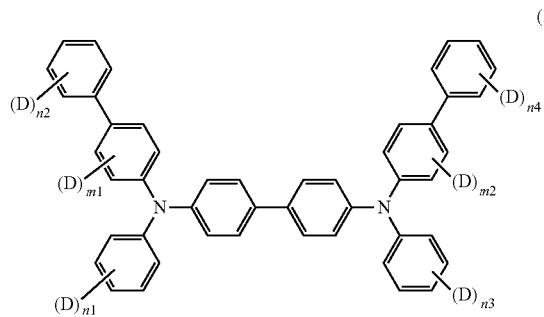

(1')

(In the formula, D represents a deuterium atom, n1 to n4 may be the same or different, and represent 0 or 5, and m1 and m2 may be the same or different, and represent 0 or 4.)

[Chemical Formula 14]

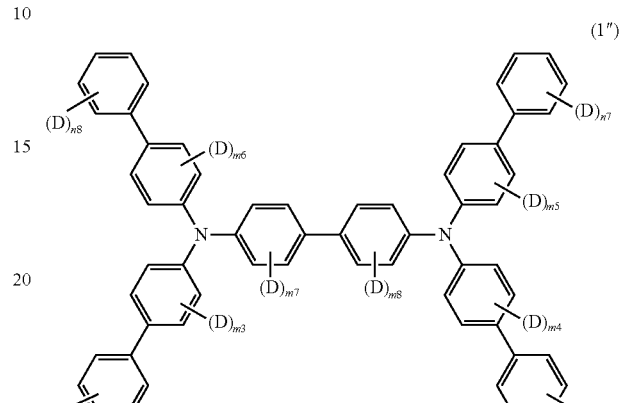

(1")

(In the formula, D represents a deuterium atom, n5 to n8 may be the same or different, and represent 0 or 5, and m3 to m8 may be the same or different, and represent 0 or 4.)

Further, among the arylamine compounds of the general formula (2), the arylamine compounds of the following general formula (2') are preferably used for an organic EL device.

[Chemical Formula 15]

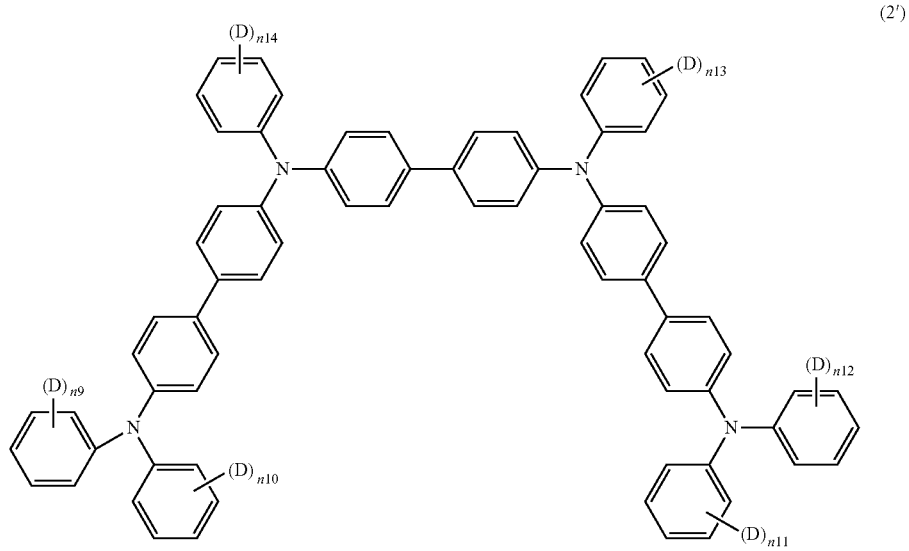

(2')

(In the formula, D represents a deuterium atom, and n9 to n14 may be the same or different, and represent 0 or 5.)

It is preferable in the present invention that at least one of R1 to R109 in the general formula (1) or (2) be a deuterium atom, or a substituent that contains a deuterium atom. Further preferably, the deuterium atom, or the substituent that contains a deuterium atom be contained in as large numbers as possible. For example, it is preferable that all of R1 to R5, all of R6 to R10, all of R11 to R14, all of R15 to R18, all of R19 to R23, or all of R24 to R28 in general formula (1) be substituted with deuterium atoms, and that all of R56 to R60, all of R61 to R64, all of R65 to R68, all of R69 to R73, all of R74 to R78, all of R79 to R82, all of R83 to R86, all of R87 to R91, all of R92 to R95, all of R96 to R99, all of R100 to R104, or all of R105 to R109 in general formula (2) be substituted with deuterium atoms. Further, it is preferable that the substituents R1 to R109 in the general formula (1) or (2) be aromatic hydrocarbon groups, aromatic heterocyclic groups, condensed polycyclic aromatic groups, or aryloxy fully substituted with deuterium atoms except at the position attached to the triphenylamine structure. Further, when A1 or A2 in the general formula (1) or (2) is represented by the structural formula (B), (C), (D), or (F), it is preferable that all of R29 to R32, all of R33 to R42, all of R43 to R46, all of R47 to R50, or all of R51 to R55 be substituted with deuterium atoms.

The arylamine compounds of general formula (1) or (2) having a triphenylamine structure according to the present invention are novel compounds, and have thin-film stability and heat resistance comparable to or better than those of conventional hole transport materials.

The arylamine compounds of general formula (1) or (2) having a triphenylamine structure according to the present invention can be used as constituent materials of the hole injection layer and/or the hole transport layer, and the electron blocking layer of an organic EL device. The arylamine compounds can be preferably used because of the high hole injectability and high hole mobility. Because of the high thin-film stability and excellent heat resistance, the arylamine compounds cannot only provide high luminous efficiency, but improve the durability of an organic EL device.

It is preferable in the organic EL device of the present invention that compounds of the following general formula (3) having a substituted anthracene ring structure and a pyridoindole ring structure be used as constituent material of the electron transport layer.

[Chemical Formula 16]

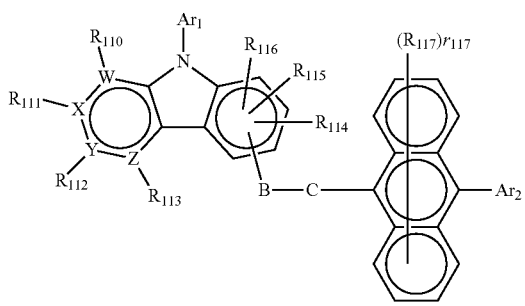

(3)

(In the formula, Ar1 and Ar2 may be the same or different. An represents a substituted or unsubstituted aromatic hydrocarbon group, a substituted or unsubstituted aromatic heterocyclic group, or a substituted or unsubstituted condensed polycyclic aromatic group, and Ar2 represents a substituted or unsubstituted aromatic hydrocarbon group, or a substituted or unsubstituted condensed polycyclic aromatic group. B and C may be the same or different, and represent a single bond, or a divalent group of a substituted or unsubstituted aromatic hydrocarbon group, a divalent group of a substituted or unsubstituted aromatic heterocyclic ring, or a divalent group of a substituted or unsubstituted condensed polycyclic aromatic group. R110 to R116 may be the same or different, and represent hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group. R117 represents a deuterium atom, a fluorine atom, a chlorine atom, cyano, trifluoromethyl, or linear or branched alkyl of 1 to 6 carbon atoms. r117 represents 0 or an integer of 1 to 8. A plurality of R117 may be the same or different when r117 is 2 or more, and the substituent R117 does not exist when r117 is 0. W, X, Y, and Z represent a carbon atom or a nitrogen atom, where only one of W, X, Y, and Z is a nitrogen atom, and, in this case, the nitrogen atom does not have the hydrogen atom or substituent for R110 to R113.)

Specific examples of the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by Ar1 in the general formula (3) include phenyl, biphenylyl, terphenylyl, tetrakisphenyl, styryl, naphthyl, anthryl, acenaphthenyl, phenanthryl, fluorenyl, indenyl, pyrenyl, pyridyl, triazinyl, pyrimidyl, furanyl, pyronyl, thienyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, naphthyridinyl, phenanthrolinyl, and acridinyl.

Specific examples of the substituent in the "substituted aromatic hydrocarbon group", "substituted aromatic heterocyclic group", or "substituted condensed polycyclic aromatic group" represented by Ar1 in the general formula (3) include a deuterium atom, a fluorine atom, a chlorine atom, cyano, trifluoromethyl, hydroxyl, nitro, linear or branched alkyl of 1 to 6 carbon atoms, cyclopentyl, cyclohexyl, linear or branched alkoxy of 1 to carbon atoms, dialkylamino groups substituted with linear or branched alkyl of 1 to 6 carbon atoms, phenyl, naphthyl, anthryl, fluorenyl, styryl, pyridyl, pyridoindolyl, quinolyl, and benzothiazolyl. These substituents may be further substituted.

Specific examples of the "aromatic hydrocarbon group" or "condensed polycyclic aromatic group" in the "substituted or unsubstituted aromatic hydrocarbon group" or "substituted or unsubstituted condensed polycyclic aromatic group" represented by Ar2 in the general formula (3) include phenyl, biphenylyl, terphenylyl, naphthyl, anthryl, phenanthryl, fluorenyl, indenyl, and pyrenyl.

Specific examples of the substituent in the "substituted aromatic hydrocarbon group" or "substituted condensed polycyclic aromatic group" represented by Ar2 in the general formula (3) include a deuterium atom, a fluorine atom, a chlorine atom, cyano, trifluoromethyl, hydroxyl, nitro, linear or branched alkyl of 1 to 6 carbon atoms, cyclopentyl, cyclohexyl, linear or branched alkoxy of 1 to 6 carbon atoms, dialkylamino groups substituted with linear or branched alkyl of 1 to 6 carbon atoms, phenyl, naphthyl, anthryl, fluorenyl, styryl, pyridyl, pyridoindolyl, quinolyl, and benzothiazolyl. These substituents may be further substituted.

Specific examples of the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by R110 to R116 in the general formula (3) include phenyl, biphenylyl, terphenylyl, tetrakisphenyl, styryl, naphthyl, anthryl, acenaphthenyl, fluorenyl, phenanthryl, indenyl, pyrenyl, pyridyl, triazinyl, pyrimidyl, furanyl, pyronyl, thienyl, quinolyl, isoquinolyl, benzofuranyl, benzothienyl, indolyl, carbazolyl, benzooxazolyl, benzothiazolyl, quinoxalyl, benzoimidazolyl, pyrazolyl, dibenzofuranyl, dibenzothienyl, naphthyridinyl, phenanthrolinyl, acridinyl, and pyridoindolyl.

Specific examples of the substituent in the "substituted aromatic hydrocarbon group", "substituted aromatic heterocyclic group", or "substituted condensed polycyclic aromatic group" represented by R110 to R116 in the general formula (3) include a deuterium atom, a fluorine atom, a chlorine atom, trifluoromethyl, linear or branched alkyl of 1 to 6 carbon atoms, phenyl, biphenylyl, terphenylyl, tetrakisphenyl, styryl, naphthyl, fluorenyl, phenanthryl, indenyl, pyrenyl, and pyridoindolyl. These substituents may be further substituted.

Specific examples of the "linear or branched alkyl of 1 to 6 carbon atoms" represented by R110 to R117 in the general formula (3) include methyl, ethyl, n-propyl, i-propyl, n-butyl, i-butyl, t-butyl, n-pentyl, i-pentyl, t-pentyl, n-hexyl, i-hexyl, and t-hexyl.

Specific examples of the "divalent group of an aromatic hydrocarbon group", "divalent group of an aromatic heterocyclic ring", or "divalent group of a condensed polycyclic aromatic group" in the "divalent group of a substituted or unsubstituted aromatic hydrocarbon group", "divalent group of a substituted or unsubstituted aromatic heterocyclic ring", or "divalent group of a substituted or unsubstituted condensed polycyclic aromatic group" represented by B or C in the general formula (3) include phenylene, biphenylylene, terphenylylene, tetrakisphenylene, naphthylene, anthrylene, phenanthrylene, fluorenylene, phenanthrolylene, indenylene, pyrenylene, pyridinylene, pyrimidinylene, quinolylene, isoquinolylene, indolylene, carbazolylene, quinoxalylene, benzoimidazolylene, pyrazolylene, naphthyridinylene, phenanthrolinylene, and acridinylene.

Specific examples of the substituent in the "divalent group of a substituted aromatic hydrocarbon group", "divalent group of a substituted aromatic heterocyclic ring", or "divalent group of a substituted condensed polycyclic aromatic group" represented by B or C in the general formula (3) include a deuterium atom, a fluorine atom, a chlorine atom, cyano, trifluoromethyl, linear or branched alkyl of 1 to 6 carbon atoms, phenyl, biphenylyl, terphenylyl, tetrakisphenyl, styryl, naphthyl, fluorenyl, phenanthryl, indenyl, pyrenyl, and pyridoindolyl. These substituents may be further substituted.

Advantage of the Invention

The arylamine compounds of general formula (1) or (2) having a triphenylamine structure are useful as constituent material of the hole injection layer, the hole transport layer, and the electron blocking layer of an organic EL device. The compounds have high hole injectability and transportability with an excellent electron blocking ability, and have a stable thin-film state and excellent heat resistance. The organic EL device of the present invention has high luminous efficiency and high power efficiency, and can thus lower the actual driving voltage of the device. Further, the turn on voltage can be lowered to improve durability. The lifetime of the organic EL device can thus be dramatically improved. It is preferable that compounds of the general formula (3) having a substituted anthracene ring structure and a pyridoindole ring structure be used as constituent material of the electron transport layer.

MODE FOR CARRYING OUT THE INVENTION

Figure 1:
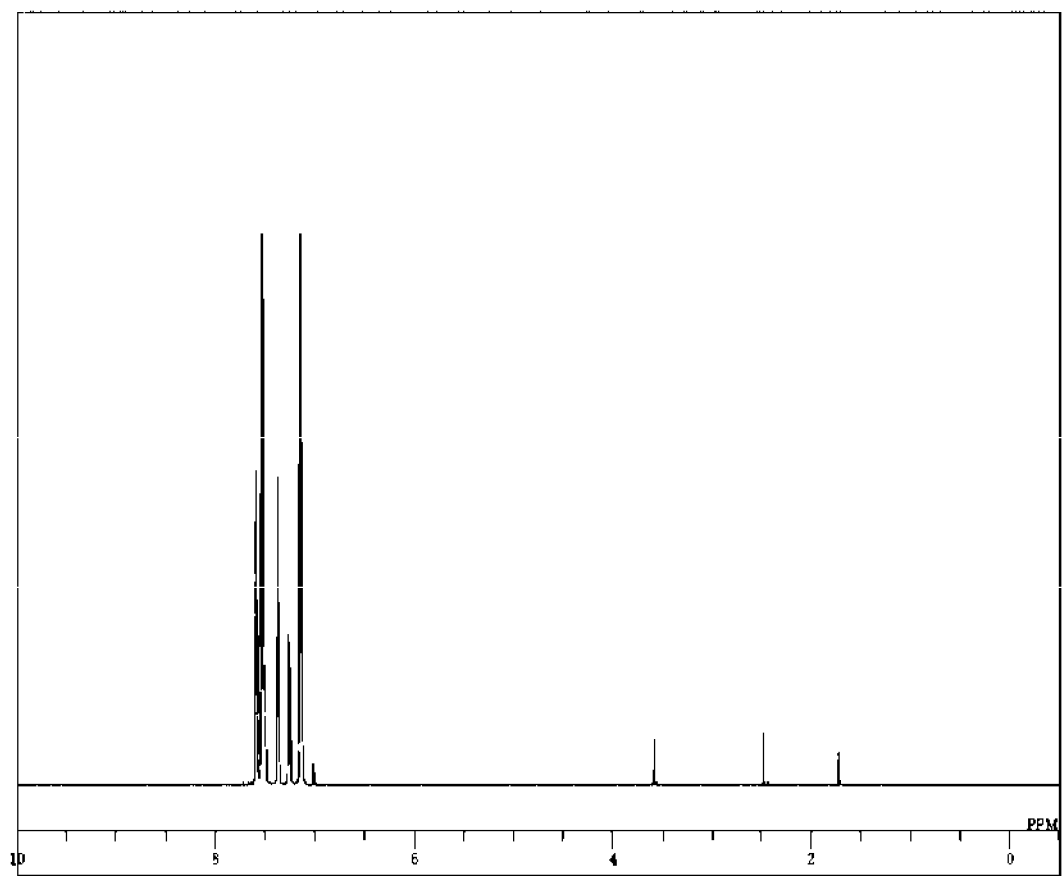
FIG. 1 is a $^1$H-NMR chart of the compound of Example 1 of the present invention (Compound 5).

The arylamine compounds having a triphenylamine structure according to the present invention are novel compounds, and may be synthesized with deuterated material by using known methods (see, for example, Patent Documents 1 and 5).

The following presents specific examples of preferred compounds among the arylamine compounds of general formula (1) or (2) having a triphenylamine structure. The present invention, however, is not restricted to these compounds.

Hydrogen atoms are omitted in the following structural formulae.

[Chemical Formula 17]

(Compound 3)

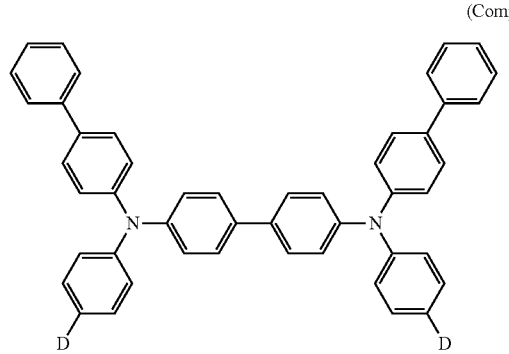

[Chemical Formula 18]

(Compound 4)

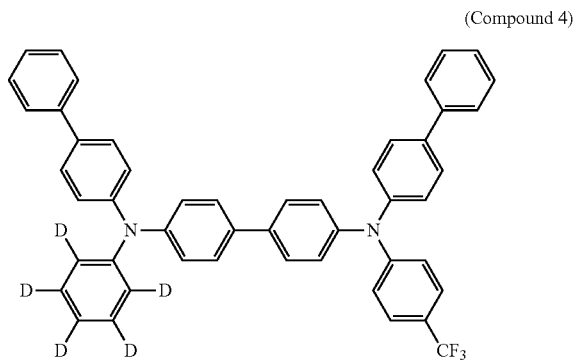

-continued
[Chemical Formula 19]
(Compound 5)
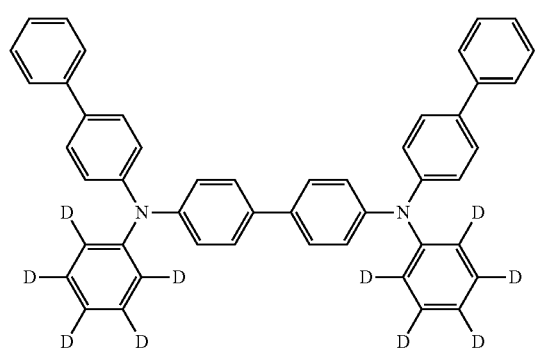
[Chemical Formula 20]
(Compound 6)
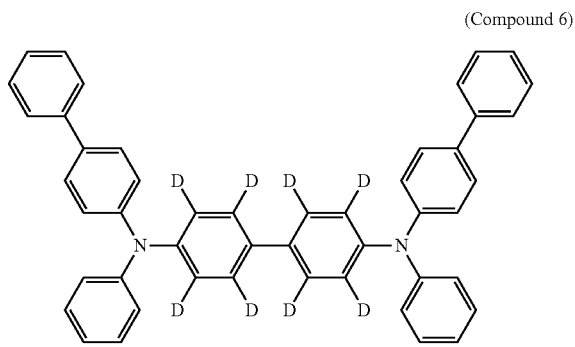
[Chemical Formula 21]
(Compound 7)
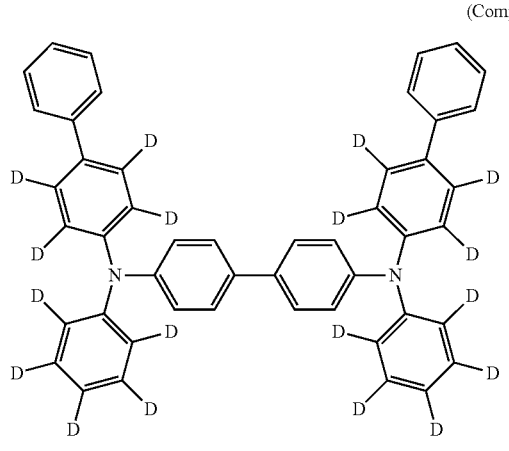
[Chemical Formula 22]
(Compound 8)
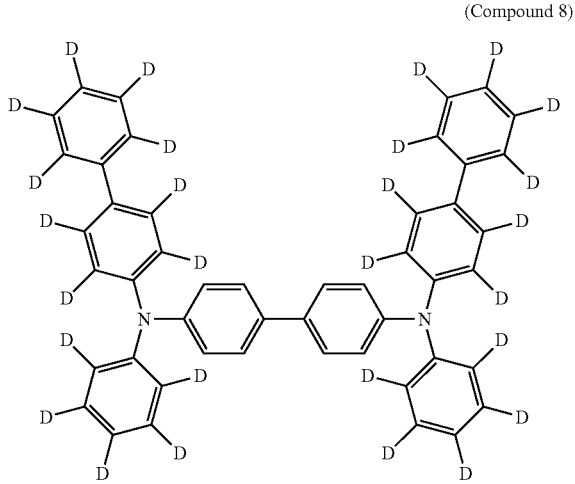
[Chemical Formula 23]
(Compound 9)
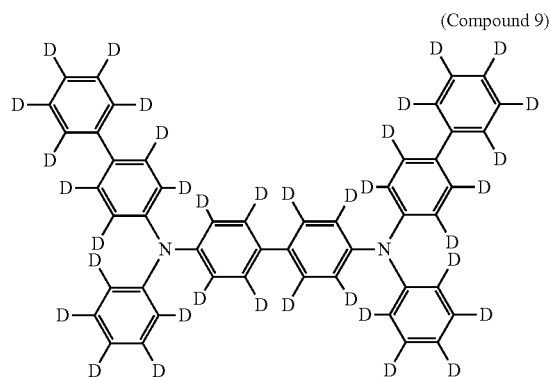
[Chemical Formula 24]
(Compound 10)
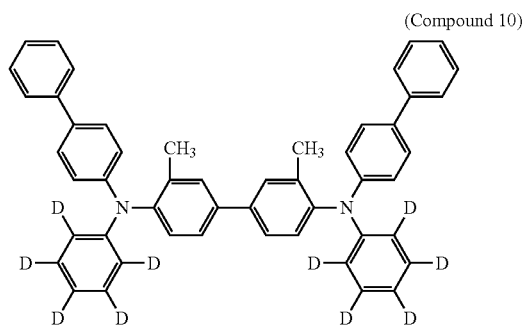

-continued
[Chemical Formula 25]
(Compound 11)
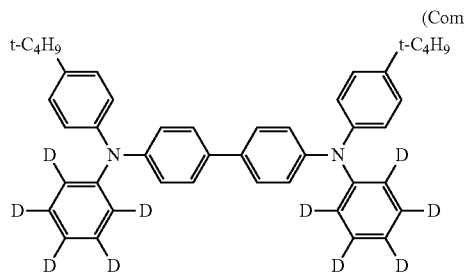
[Chemical Formula 26]
(Compound 12)
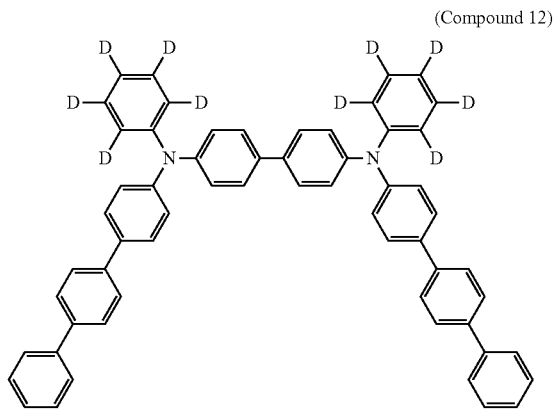
[Chemical Formula 27]
(Compound 13)
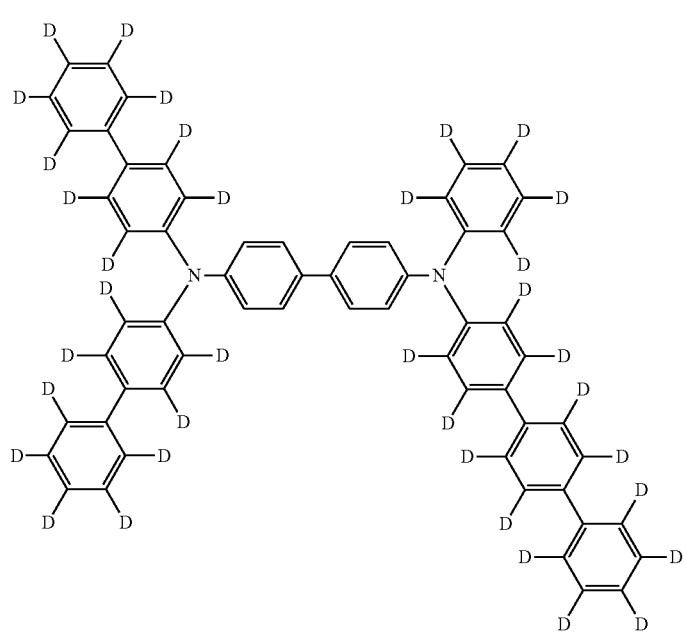
[Chemical Formula 28]
(Compound 14)
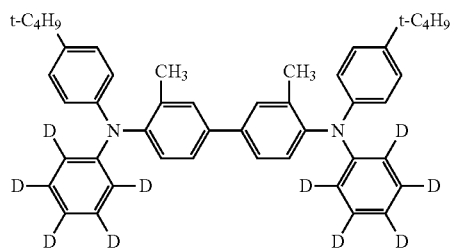
[Chemical Formula 29]
(Compound 15)
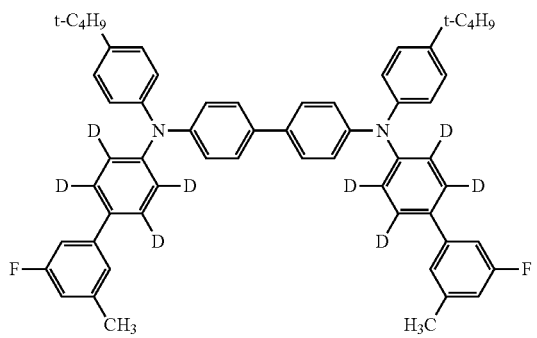

-continued
[Chemical Formula 30]
(Compound 16)
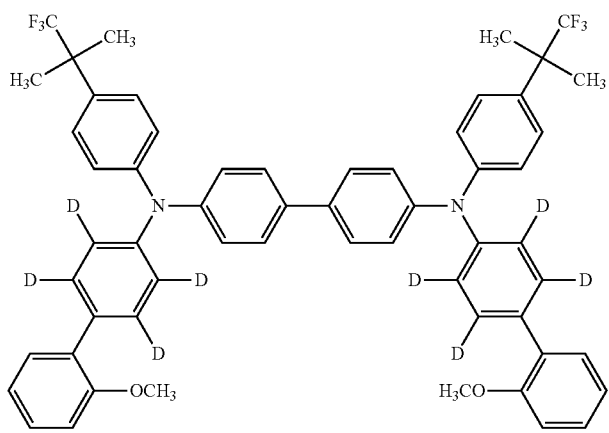
[Chemical Formula 31]
(Compound 17)
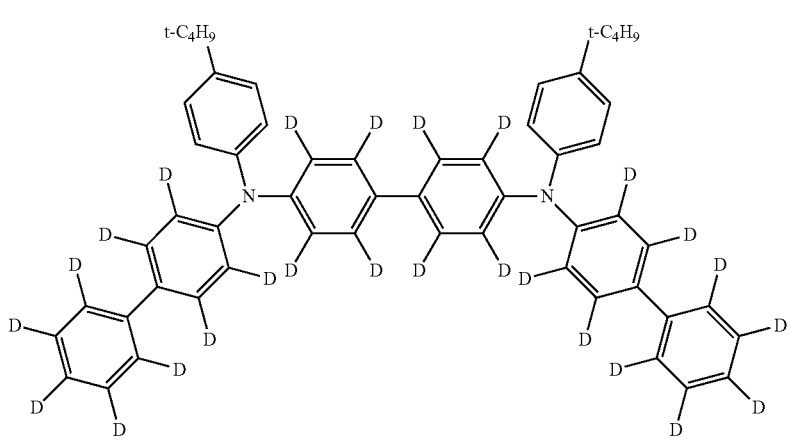
[Chemical Formula 32]
(Compound 18)
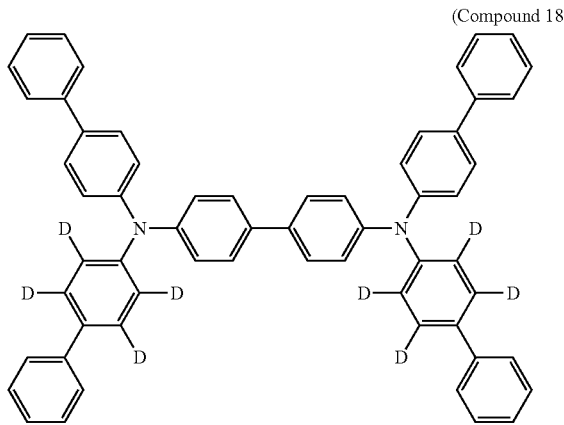
[Chemical Formula 33]
(Compound 19)
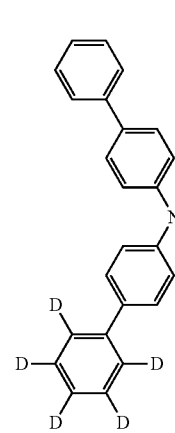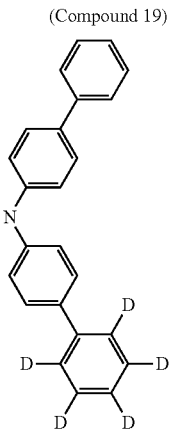

[Chemical Formula 34] (Compound 20)
[Chemical Formula 35] (Compound 21)
[Chemical Formula 36] (Compound 22)
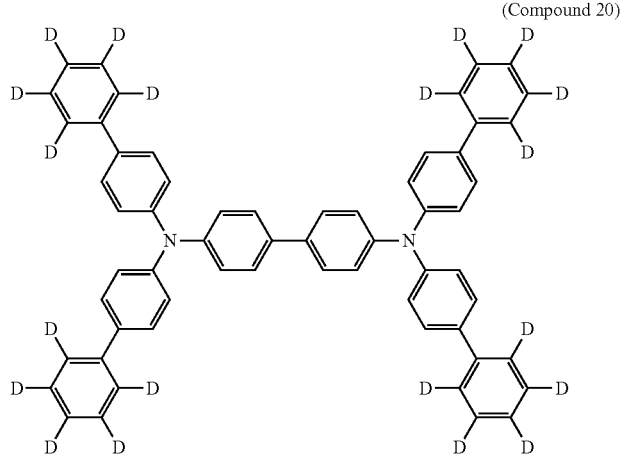

-continued
[Chemical Formula 37]
(Compound 23)
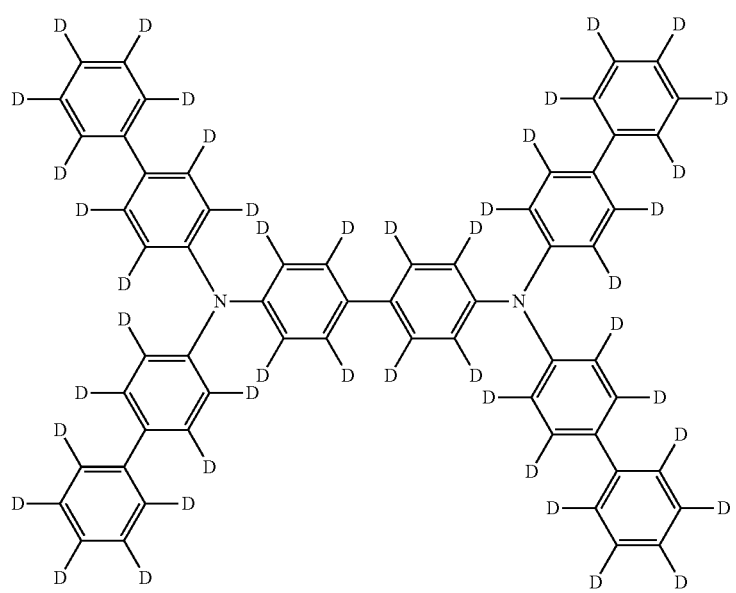
[Chemical Formula 38]
(Compound 24)
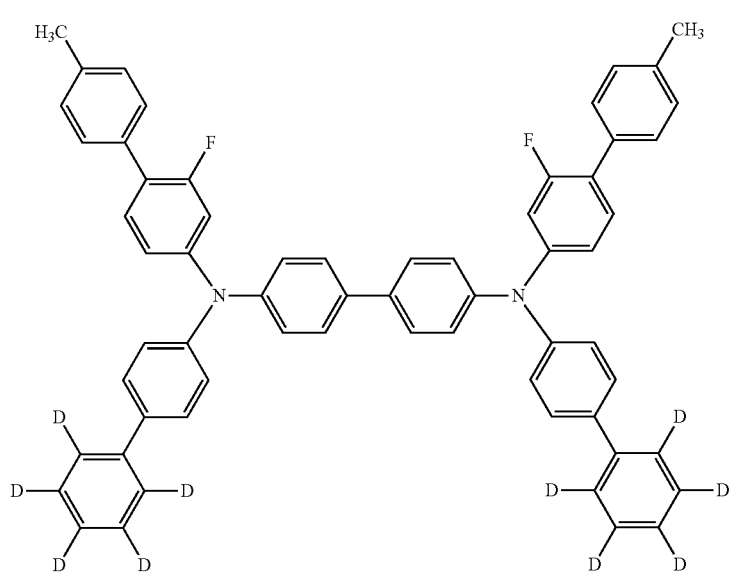

[Chemical Formula 39]
(Compound 25)
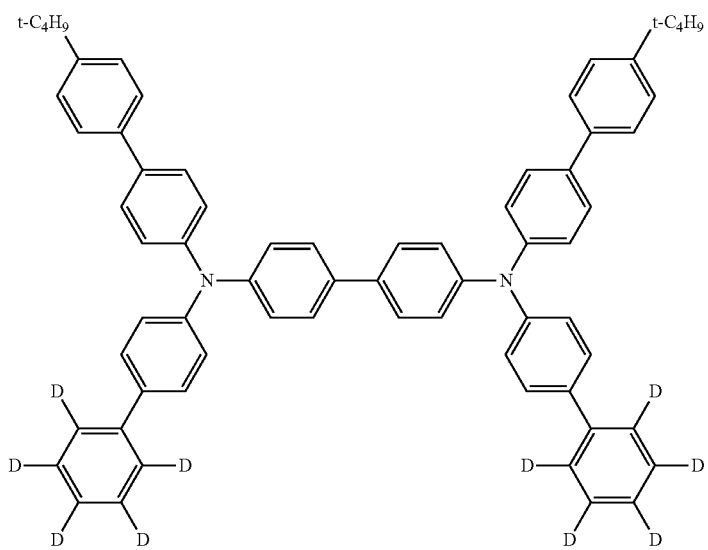
[Chemical Formula 40]
(Compound 26)
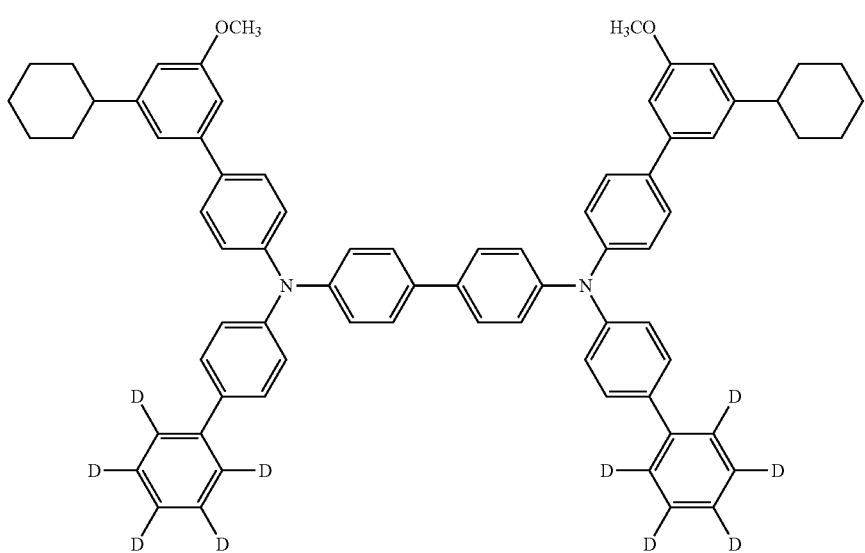

[Chemical Formula 41]
(Compound 27)
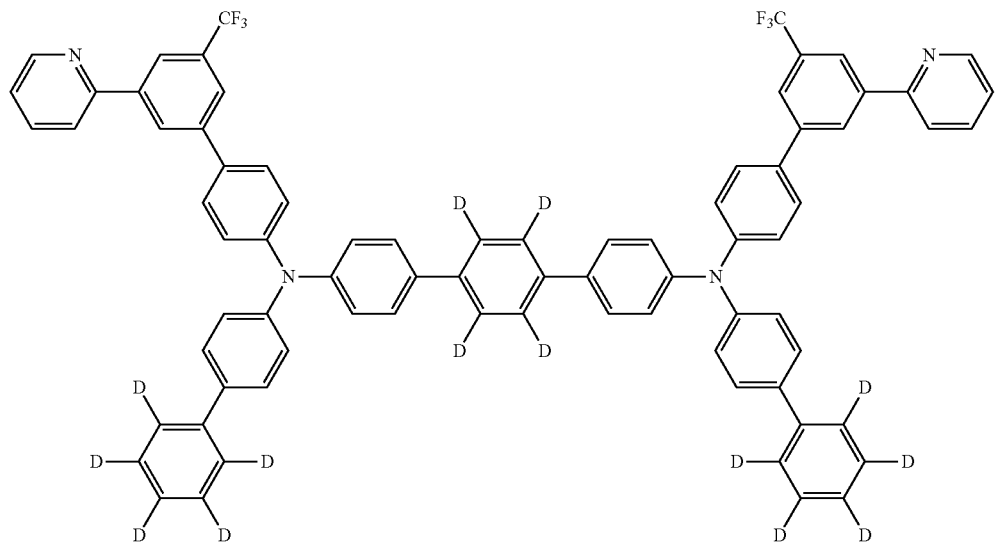
[Chemical Formula 42]
(Compound 28)
[Chemical Formula 43]
(Compound 29)
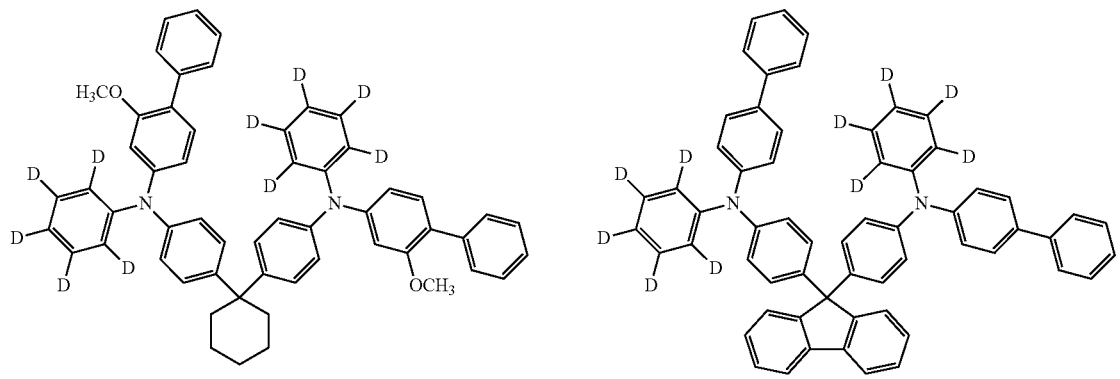
[Chemical Formula 44]
(Compound 30)
[Chemical Formula 45]
(Compound 31)
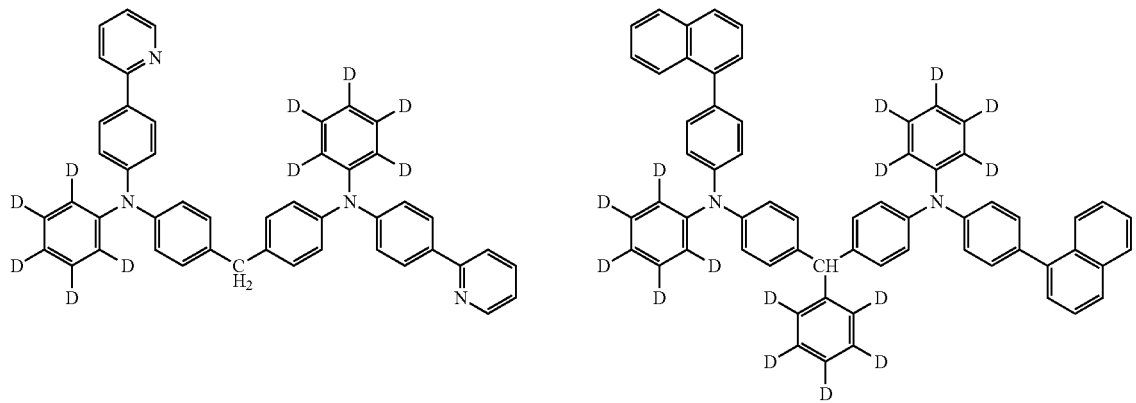

-continued
[Chemical Formula 46]
(Compound 32)
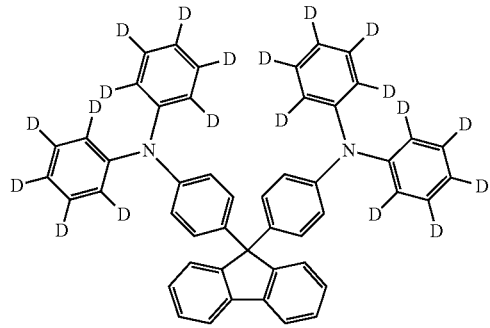
[Chemical Formula 47]
(Compound 33)
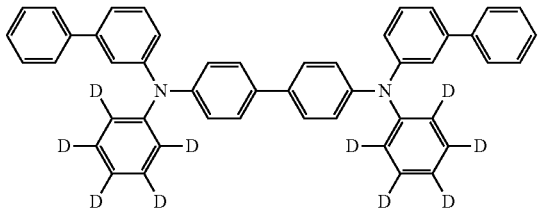
[Chemical Formula 48]
(Compound 34)
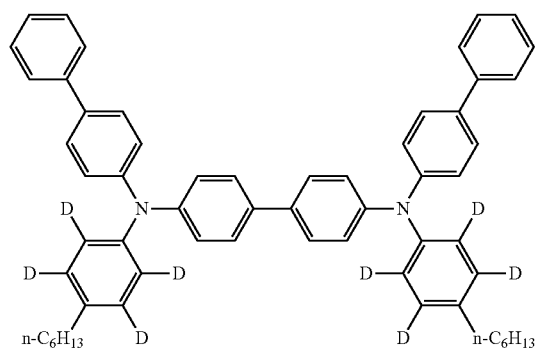
[Chemical Formula 49]
(Compound 35)
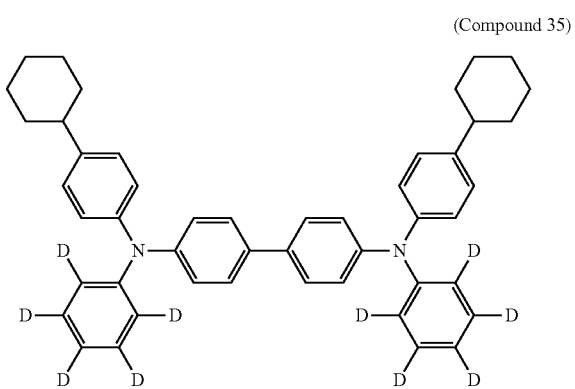
[Chemical Formula 50]
(Compound 36)
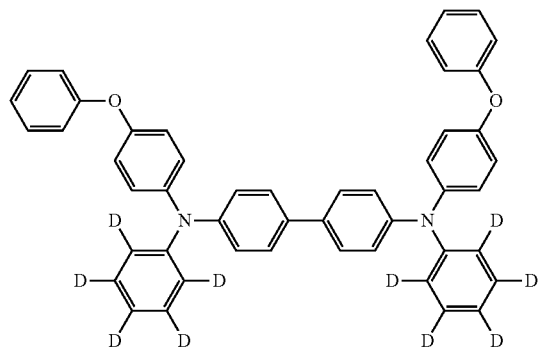
[Chemical Formula 51]
(Compound 37)
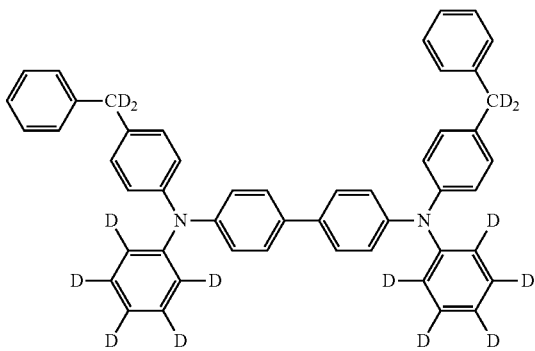
[Chemical Formula 52]
(Compound 38)
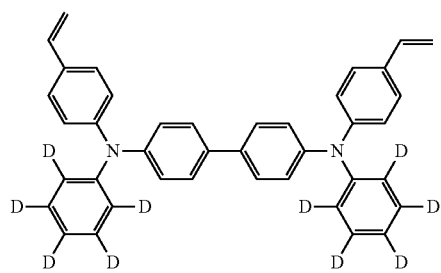
[Chemical Formula 53]
(Compound 39)
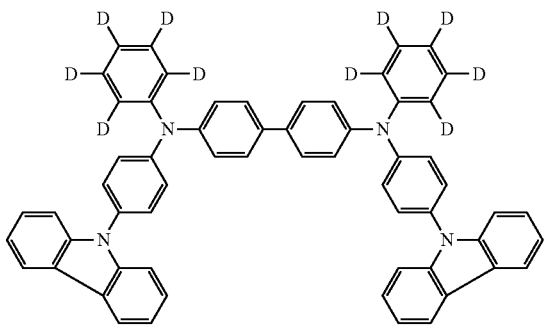

[Chemical Formula 54]
(Compound 40)
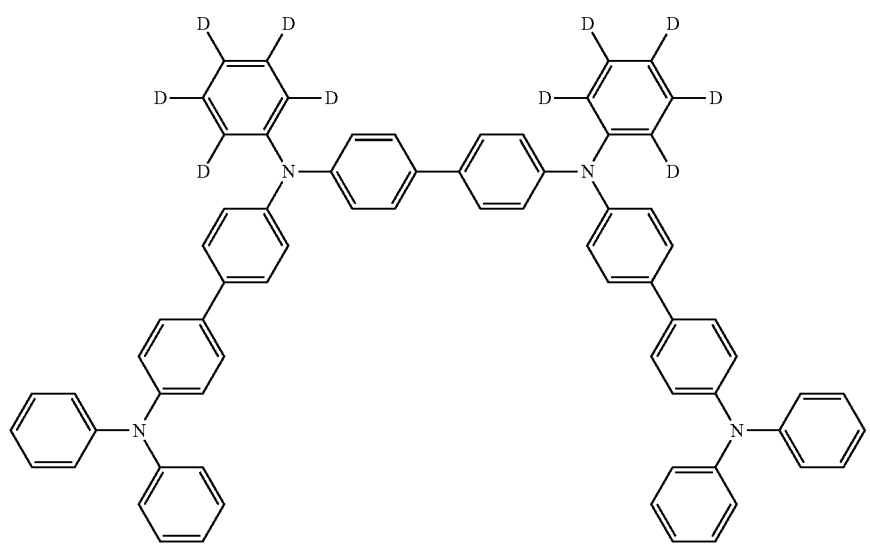
[Chemical Formula 55]
(Compound 41)
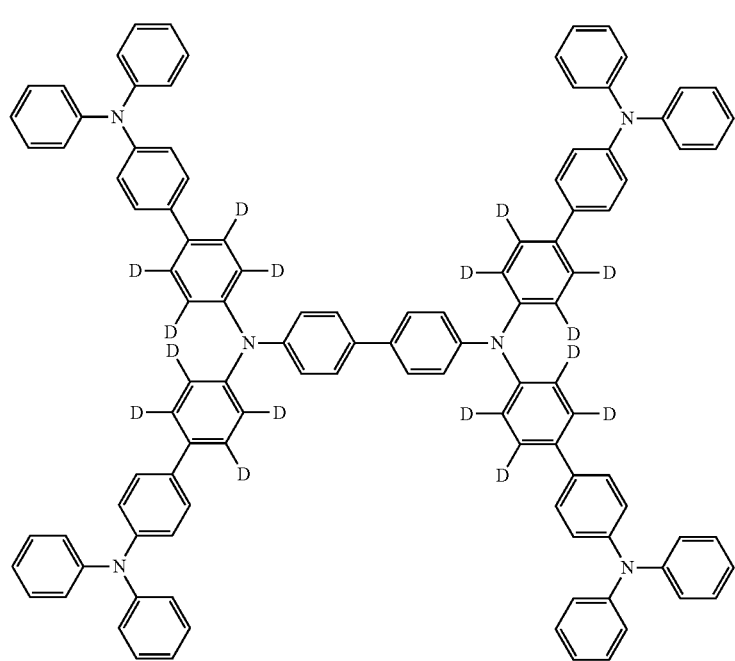

[Chemical Formula 56]
(Compound 42)
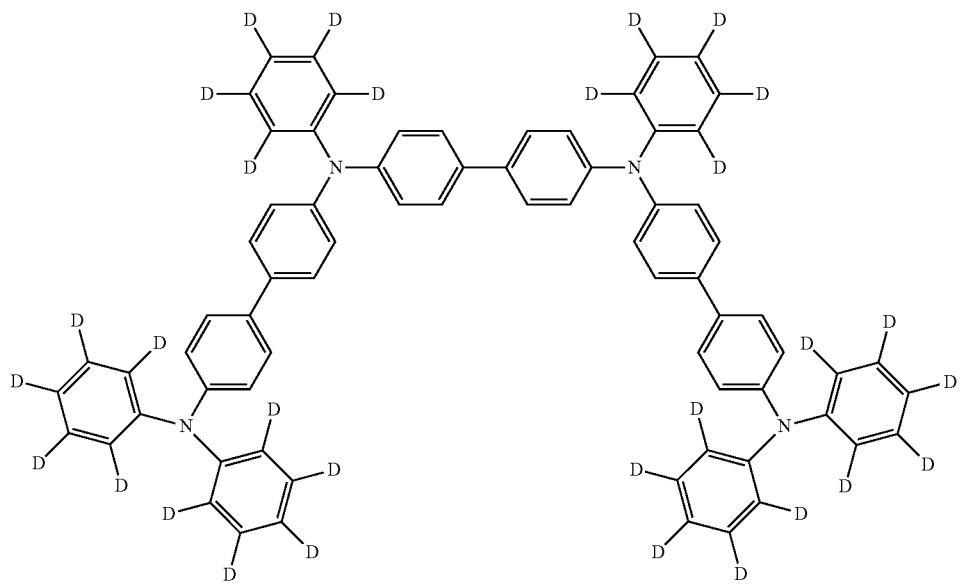
[Chemical Formula 57]
(Compound 43)
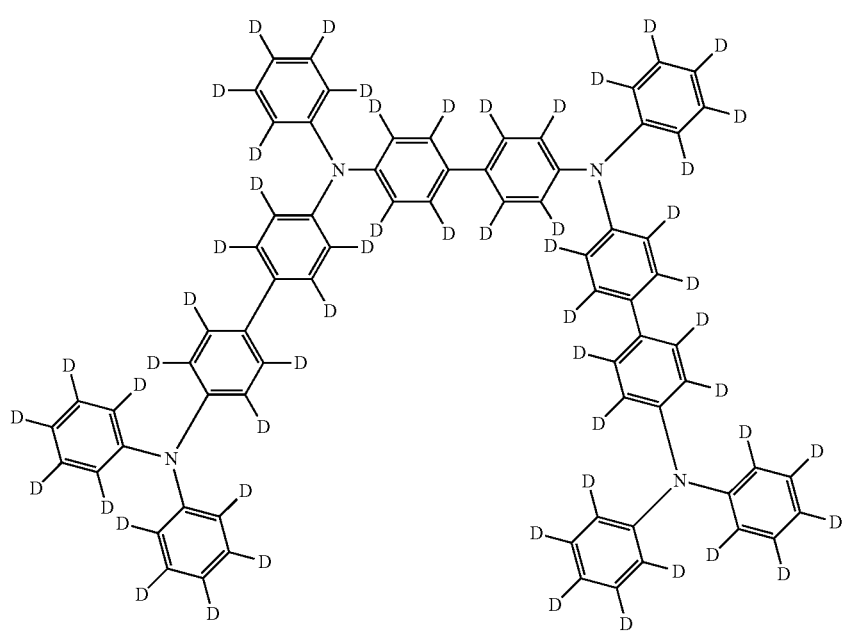

[Chemical Formula 58]
(Compound 44)
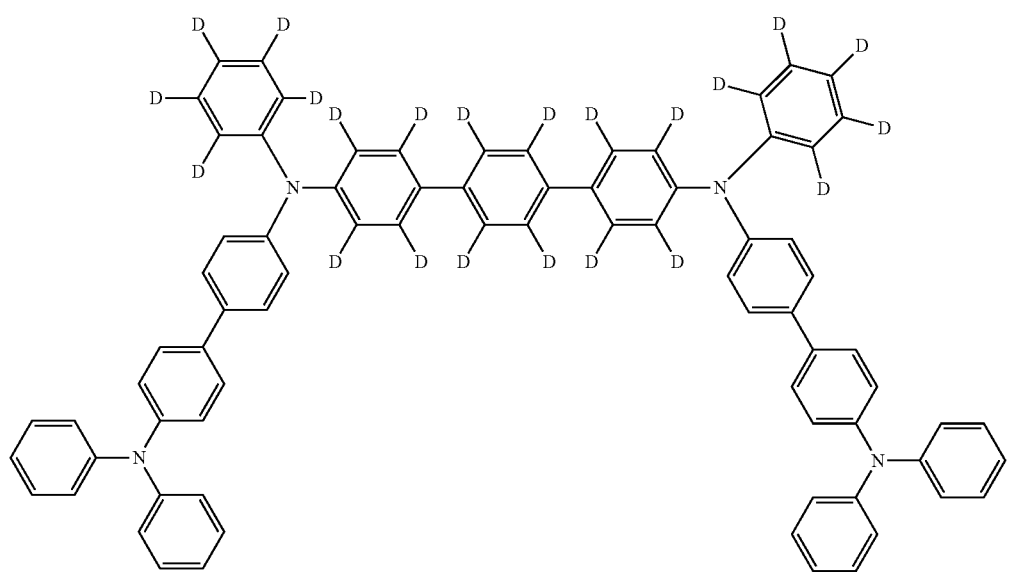
[Chemical Formula 59]
(Compound 45)
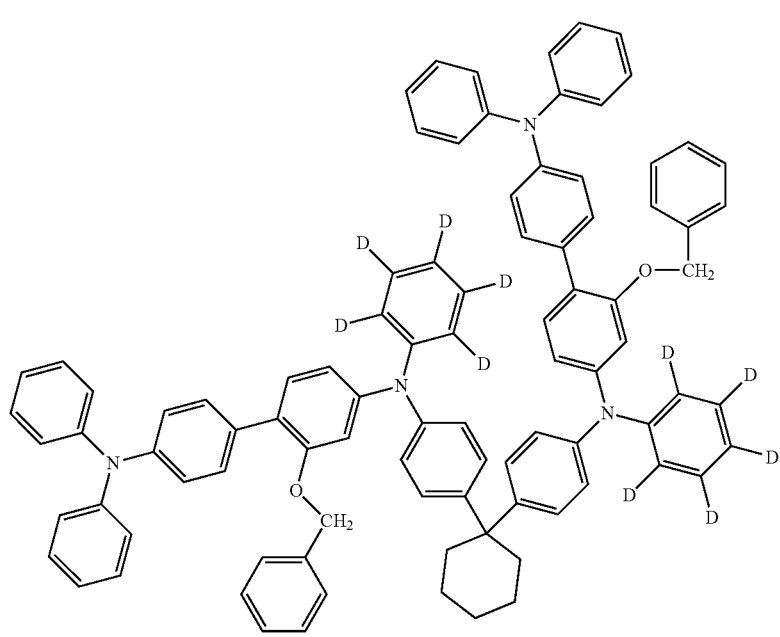

[Chemical Formula 60]
(Compound 46)
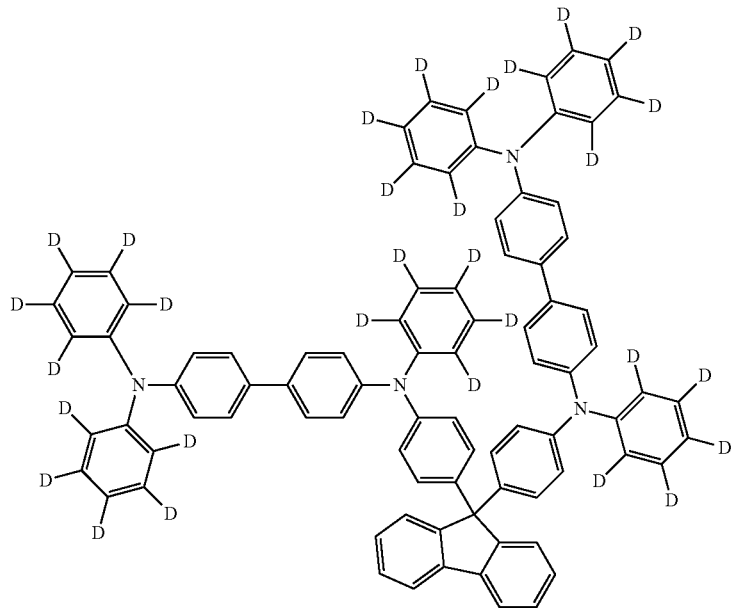
[Chemical Formula 61]
(Compound 47)
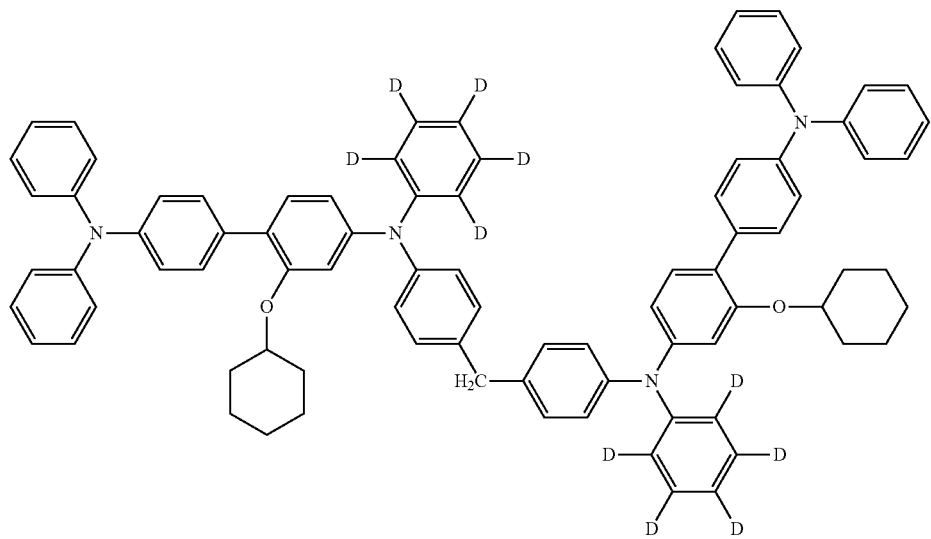

[Chemical Formula 62]

(Compound 48)

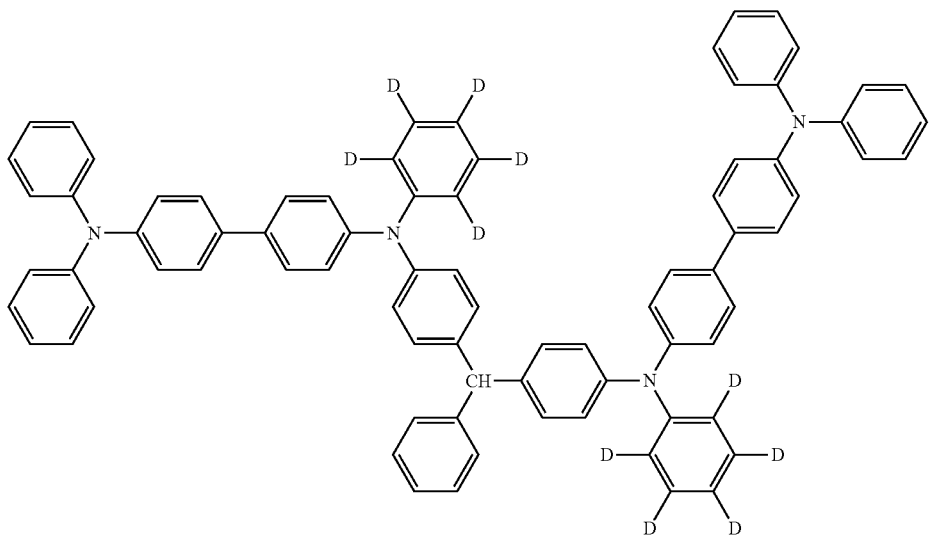

[Chemical Formula 63]

(Compound 49)

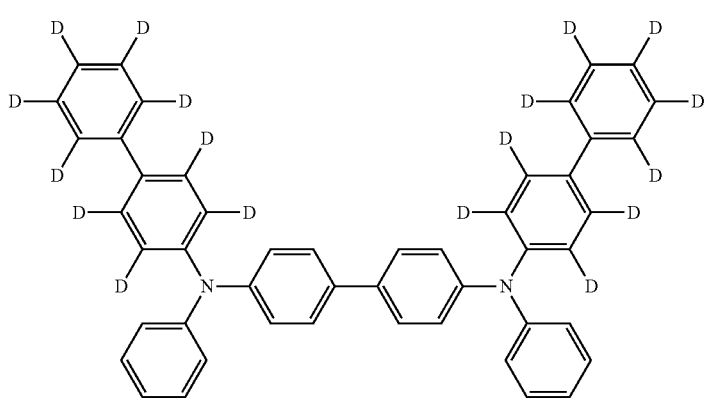

These compounds were purified by methods such as column chromatography, adsorption using, for example, a silica gel, activated carbon, or activated clay, and recrystallization or crystallization using a solvent. The compounds were identified by NMR analysis. Glass transition point (Tg) and work function were taken for the measurement of physical properties. Glass transition point (Tg) can be used as an index of stability in the thin-film state, and the work function as an index of hole transportability.

The glass transition point (Tg) was measured using a powder, using a high-sensitive differential scanning calorimeter DSC3100S produced by Bruker AXS.

For the measurement of work function, a 100 nm-thick thin film was fabricated on an ITO substrate, and an atmosphere photoelectron spectrometer AC-2 produced by Riken Keiki Co., Ltd. was used.

The organic EL device of the present invention may have a structure including an anode, a hole transport layer, an electron blocking layer, a light emitting layer, an electron transport layer, and a cathode successively formed on a substrate, optionally with a hole injection layer between the anode and the hole transport layer, or with an electron injection layer between the electron transport layer and the cathode. Some of the organic layers in this multilayer structure may be omitted. For example, the organic EL device may be structured to include an anode, a hole transport layer, a light emitting layer, an electron transport layer, and a cathode successively formed on a substrate.

Electrode materials with a large work function, such as ITO and gold, are used as the anode of the organic EL device of the present invention. The hole injection layer of the organic EL device of the present invention may be made of a material, the examples of which include porphyrin compounds as represented by copper phthalocyanine, starburst-type triphenylamine derivatives, various triphenylamine tetramers, accepting heterocyclic compounds such as hexacyano azatriphenylene, and coating-type polymer materials, in addition to the arylamine compounds of general formula (1) or (2) having a triphenylamine structure of the present invention. These materials may be formed into a thin film by using a vapor deposition method, or other known methods such as spin coating and an inkjet method.

Examples of the material used for the hole transport layer of the organic EL device of the present invention include benzidine derivatives such as N,N'-diphenyl-N,N'-di(m-tolyl)benzidine (hereinafter, "TPD"), N,N'-diphenyl-N,N'-di(α-naphthyl)benzidine (hereinafter, "NPD"), and N,N,N',N'-tetrabiphenylylbenzidine, 1,1-bis[4-(di-4-tolylamino)phenyl]cyclohexane (hereinafter, "TAPC"), and various triphenylamine trimers and tetramers, in addition to the arylamine compounds of general formula (1) or (2) having a triphenylamine structure of the present invention. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer. Examples of the material used for the hole injection/transport layer include coating-type polymer materials such as poly(3, 4-ethylenedioxythiophene) (hereinafter, simply "PEDOT")/poly(styrene sulfonate) (hereinafter, simply "PSS"). These materials may be formed into a thin-film by using a vapor deposition method, or other known methods such as spin coating and an inkjet method.

Further, the hole injection layer or the hole transport layer may be one obtained by the P-doping of material such as trisbromophenylamine hexachloroantimony in the material commonly used for these layers. Further, for example, polymer compounds having a TPD structure as a part of the compound structure also may be used.

Examples of the material used for the electron blocking layer of the organic EL device of the present invention include compounds having an electron blocking effect, including, for example, carbazole derivatives such as 4,4',4"-tri(N-carbazolyl)triphenylamine (hereinafter, simply "TCTA"), 9,9-bis[4-(carbazol-9-yl)phenyl]fluorene, 1,3-bis(carbazol-9-yl)benzene (hereinafter, simply "mCP"), and 2,2-bis(4-carbazol-9-ylphenyl)adamantane (hereinafter, simply "Ad-Cz"); and compounds having a triphenylsilyl group and a triarylamine structure, as represented by 9-[4-(carbazol-9-yl)phenyl]-9-[4-(triphenylsilyl)phenyl]-9H-fluorene, in addition to the arylamine compounds of general formula (1) or (2) having a triphenylamine structure of the present invention. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer. These materials may be formed into a thin-film by using a vapor deposition method, or other known methods such as spin coating and an inkjet method.

Examples of the material used for the light emitting layer of the organic EL device of the present invention include various metal complexes, anthracene derivatives, bis(styryl)benzene derivatives, pyrene derivatives, oxazole derivatives, and polyparaphenylene vinylene derivatives, in addition to quinolinol derivative metal complexes such as $Alq_3$. Further, the light emitting layer may be configured from a host material and a dopant material. Examples of the host material include thiazole derivatives, benzimidazole derivatives, and polydialkyl fluorene derivatives, in addition to the foregoing light-emitting materials. Examples of the dopant material include quinacridone, coumarin, rubrene, perylene, derivatives thereof, benzopyran derivatives, rhodamine derivatives, and aminostyryl derivatives. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer.

Further, the light-emitting material may be phosphorescent light-emitting material. Phosphorescent materials as metal complexes of metals such as iridium and platinum may be used as the phosphorescent light-emitting material. Examples of the phosphorescent materials include green phosphorescent materials such as $Ir(ppy)_3$, blue phosphorescent materials such as FIrpic and $FIr_6$, and red phosphorescent materials such as $Btp_2Ir(acac)$. Here, carbazole derivatives such as 4,4'-di(N-carbazolyl)biphenyl (hereinafter, simply "CBP"), TCTA, and mCP may be used as the hole injecting and trans-porting host material. Compounds such as p-bis(triphenylsilyl)benzene (hereinafter, simply "UGH2"), and 2,2',2"-(1,3,5-phenylene)-tris(1-phenyl-1H-benzimidazole) (hereinafter, simply "TPBI") represented by the following formula may be used as the electron transporting host material.

[Chemical Formula 64]

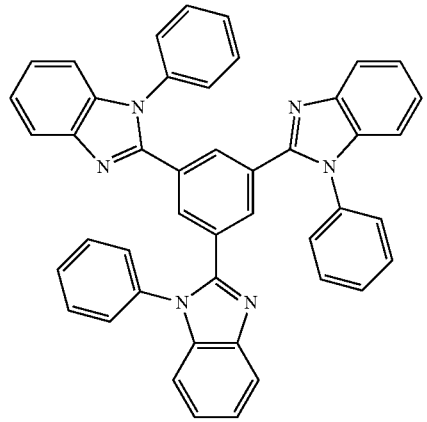

In order to avoid concentration quenching, the doping of the host material with the phosphorescent light-emitting material is preferably made by co-evaporation in a range of 1 to 30 weight percent with respect to the whole light emitting layer.

These materials may be formed into a thin-film by using a vapor deposition method, or other known methods such as spin coating and an inkjet method.

The hole blocking layer of the organic EL device of the present invention may be formed by using hole blocking compounds such as various rare earth complexes, triazole derivatives, and triazine derivatives, and oxadiazole derivatives, in addition to phenanthroline derivatives such as bathocuproin (hereinafter, simply "BCP"), and the metal complexes of quinolinol derivatives such as aluminum(III) bis(2-methyl-8-quinolinate)-4-phenylphenolate (hereinafter, simply "BAlq"). These materials may also serve as the material of the electron transport layer. These may be individually deposited for film forming, or may be used as a single layer deposited as a mixture with other materials, or as a laminate of individually deposited layers, a laminate of layers deposited as a mixture, or a laminate of layers deposited by being mixed with an individually deposited layer. These materials may be formed into a thin-film by using a vapor deposition method, or other known methods such as spin coating and an inkjet method.

Examples of the material used for the electron transport layer of the organic EL device of the present invention include various metal complexes, triazole derivatives, triazine derivatives, oxadiazole derivatives, thiadiazole derivatives, carbodiimide derivatives, quinoxaline derivatives, phenanthroline derivatives, and silole derivatives, in addition to quinolinol derivative metal complexes such as $Alq_3$ and BAlq. These may be individually deposited for film forming, or may be used as a single layer deposited as a mixture with other materials, Or as a laminate of individually deposited layers, a laminate of layers deposited as a mixture, or a laminate of layers deposited by being mixed with an individually deposited layer. These materials may be formed into a thin-film by using a vapor deposition method, or other known methods such as spin coating and an inkjet method.

Examples of the material used for the electron injection layer of the organic EL device of the present invention include alkali metal salts (such as lithium fluoride, and cesium fluoride), alkaline earth metal salts (such as magnesium fluoride), and metal oxides (such as aluminum oxide). However, the electron injection layer may be omitted upon preferably selecting the electron transport layer and the cathode.

The cathode of the organic EL device of the present invention may be made of an electrode material having a low work function (such as aluminum), or an alloy of an electrode material having an even lower work function (such as a magnesium-silver alloy, a magnesium-indium alloy, or an aluminum-magnesium alloy).

The following describes an embodiment of the present invention in more detail based on Examples. The present invention, however, is not restricted to the following Examples.

Example 1

Synthesis of 4,4'-bis[(biphenyl-4-yl)-(phenyl-$d_5$)-amino]biphenyl (Compound 5)

Aniline-2,3,4,5,6-$d_5$ (30.00 g), and acetic acid (50 ml) were added to a nitrogen-substituted reaction vessel, and heated to 70° C. while being stirred. The mixture was further stirred at 70° C. for 4 hours after dropping acetic anhydride (34.7 ml). After being cooled to room temperature, the reaction liquid was added to ice water, and the precipitated crystals were separated by filtration to obtain pale brown crystals (48.71 g). The filtrate was transferred to a separating funnel, and subjected to an extraction procedure by addition of toluene (1,000 ml). The extract was concentrated, and dried to solidify to obtain brown crystals (4.05 g). These crystals were combined, and dried under reduced pressure to obtain brown crystals of acetanilide-2,3,4,5,6-$d_5$ (41.33 g; yield 96.5%).

The resulting acetanilide-2,3,4,5,6-$d_5$ (35.00 g), 4-bromobiphenyl (48.50 g), a copper powder (1.32 g), potassium carbonate (43.14 g), sodium sulfite (6.53 g), and dodecylbenzene (97 ml) were added to a nitrogen-substituted reaction vessel, heated, and stirred at 210° C. for 34 hours. During this procedure, a copper powder (1.32 g) and potassium carbonate (2.88 g) were added four times to continue the reaction. After cooling to 100° C., toluene (194 ml) was added. Upon further cooling to 50° C., the precipitated insoluble matter was removed by filtration.

After being concentrated, the filtrate was added to a nitrogen-substituted reaction vessel, followed by addition of potassium hydroxide (30 g), water (40 ml), and isoamyl alcohol (61 ml). The mixture was heated, and refluxed for 3 hours while being stirred. Upon cooling, the precipitated crude crystals were washed with methanol (100 ml), heated in a methanol/water mixed solvent, and stirred at 78° C. for 1 hour. The precipitated crystals were collected by filtration, and purified by recrystallization using toluene/n-hexane to obtain brown crystals of (biphenyl-4-yl)-(phenyl-$d_5$)-amine (35.78 g; yield 68.7%).

The resulting (biphenyl-4-yl)-(phenyl-$d_5$)-amine (15.00 g), 4,4'-diiodobiphenyl (10.14 g), a copper powder (0.16 g), 3,5-di(tert-butyl)salicylic acid (0.63 g), potassium carbonate (10.35 g), sodium sulfite (0.78 g), and dodecylbenzene (18 ml) were added to a nitrogen-substituted reaction vessel, heated, and stirred at 210° C. for 11 hours. During procedure, a copper powder (0.16 g) and potassium carbonate (0.35 g) were added to continue the reaction. After cooling to 100° C., toluene (269 ml) was added. Upon further cooling to 50° C., the precipitated insoluble matter was removed by filtration. The filtrate was concentrated, and purified by three runs of recrystallization using toluene/n-hexane to obtain pale yellowish white crystals of 4,4'-bis[(biphenyl-4-yl)-(phenyl-$d_5$)-amino]biphenyl (Compound 5; 14.61 g; yield 89.9%).

The structure of the resulting pale yellowish white crystals was identified by NMR. 1H-NMR measurement result is presented in FIG. 1.

1H-NMR (THF-$d_8$) detected 26 hydrogen signals, as follows. δ(ppm)=7.59 (4H), 7.53 (8H), 7.38 (4H), 7.27 (2H), 7.15 (8H)

Example 2

Synthesis of 4,4'-bis{(biphenyl-$d_9$-4-yl)-phenylamino}biphenyl (Compound 49)

Bromobenzene-$d_5$ (16.08 g), (phenyl-$d_5$)boronic acid (13.79 g), potassium carbonate (20.46 g), water (74 ml), toluene (160 ml), and ethanol (40 ml) were added to a nitrogen-substituted reaction vessel, and aerated with nitrogen gas for 30 min under ultrasonic irradiation. After adding tetrakis(triphenylphosphine)palladium (2.28 g), the mixture was heated, and stirred for 7.5 hours under reflux. The mixture was allowed to cool to room temperature, and separated to collect the organic layer. The organic layer was dried over magnesium sulfate, and concentrated to obtain a black crude product (22.27 g). The crude product was purified by column chromatography (carrier: silica gel; eluent: n-hexane) to obtain white crystals of biphenyl-$d_{10}$ (14.07 g; yield 86%).

The resulting biphenyl-$d_{10}$ (14.07 g), iron chloride(III) (0.28 g), bromine (2.2 ml), and chloroform (70 ml) were added to a nitrogen-substituted reaction vessel, and stirred at room temperature for 46 hours. After adding a 10% sodium hydroxide aqueous solution (70 ml) to the reaction solution, the mixture was stirred, and separated to collect the organic layer. After being washed with water (100 ml), the organic layer was concentrated to obtain 4-bromobiphenyl-$d_9$ (17.69 g).

The resulting 4-bromobiphenyl-$d_9$ (17.60 g), aniline (27 ml), tert-butoxy sodium (8.38 g), toluene (260 ml) were added to a nitrogen-substituted reaction vessel, and aerated with nitrogen gas for 30 min under ultrasonic irradiation. After adding tris(dibenzylideneacetone)dipalladium (0.80 g) and tri (tert-butyl)phosphine (0.9 ml), the mixture was heated, and stirred at 85° C. for 2.5 hours. The mixture was allowed to cool to room temperature, and stirred after adding methanol (10 ml) and water (200 ml). The insoluble matter was removed by filtration, and the organic layer was separated and collected. The organic layer was dried over magnesium sulfate, and concentrated to obtain a black crude product (35.17 g). The crude product was purified by column chromatography (carrier: silica gel; eluent: toluene/n-hexane) to obtain [(biphenyl-$d_9$)-4-yl]-phenylamine (8.55 g; yield, 39% in two steps).

The resulting [(biphenyl-$d_9$)-4-yl]-phenylamine (2.20 g), 4,4'-diiodobiphenyl (1.56 g), a copper powder (25.7 mg), 3,5-di(tert-butyl)salicylic acid (98.5 mg), potassium carbonate (1.59 g), sodium sulfite (112.5 mg), and dodecylbenzene (2 ml) were added to a nitrogen-substituted reaction vessel, heated, and stirred at 210° C. for 8 hours. After cooling to room temperature, toluene (40 ml) was added. The mixture was then heated to 50° C., and the insoluble matter was removed by filtration. The filtrate was concentrated, and purified by three runs of recrystallization using toluene/n-hexane. The product was then washed with methanol under reflux to obtain pale yellowish white crystals of 4,4'-bis{(biphenyl-$d_9$-4-yl)-phenylamino}biphenyl (Compound 49; 2.11 g; yield 83.4%).

Figure 2:
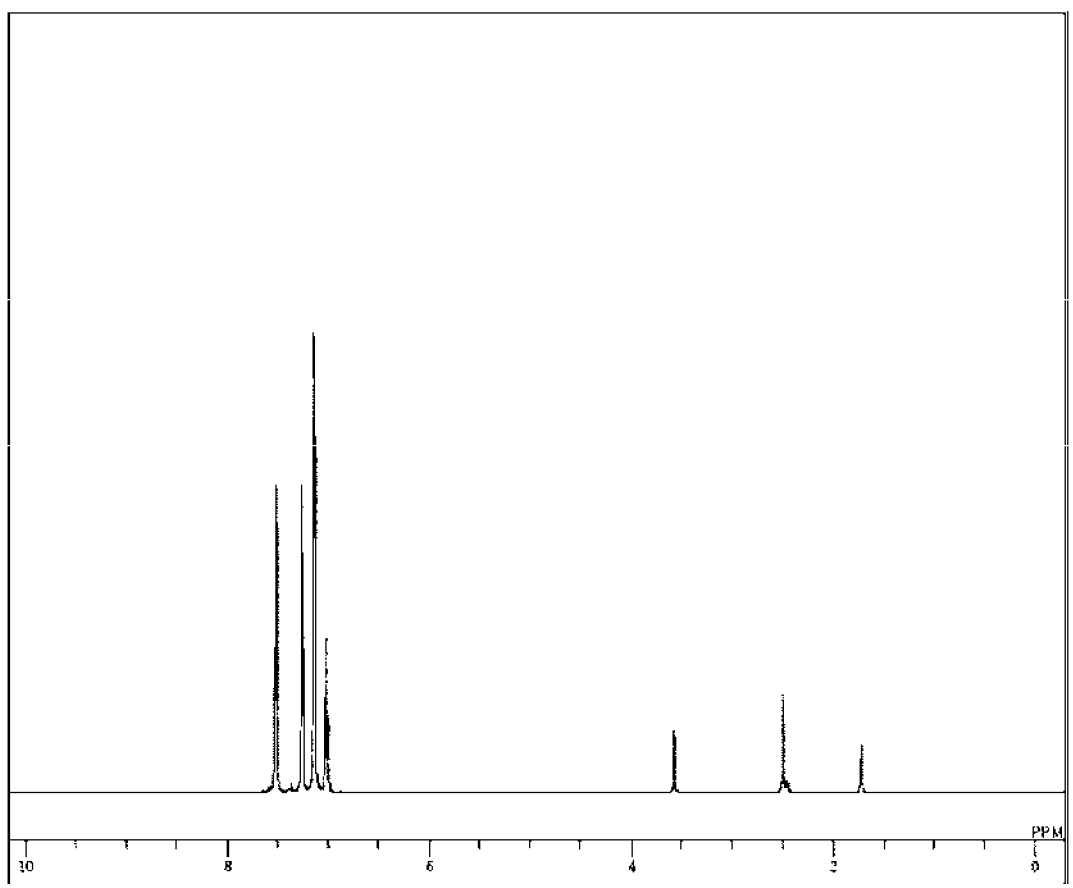
FIG. 2 is a $^1$H-NMR chart of the compound of Example 2 of the present invention (Compound 49).

The structure of the resulting pale yellowish white crystals was identified by NMR. The $^1$H-NMR measurement result is presented in FIG. 2.

1H-NMR (THF-d$_8$) detected 18 hydrogen signals, as follows. δ(ppm)=7.52 (4H), 7.26 (4H), 7.14 (8H), 7.02 (2H)

Example 3

Synthesis of 4,4'-bis{(biphenyl-4-yl)-[(biphenyl-2,3,5,6-d$_4$)-4-yl]amino}biphenyl (Compound 18)

(Biphenyl-4-yl)-(phenyl-d$_5$)amine (20.0 g) and DMF (400 ml) were added and dissolved in a nitrogen-substituted reaction vessel, and N-bromosuccinimide (4.7 g) was added under ice-cooled conditions. The reaction temperature was raised to room temperature while adding N-bromosuccinimide (9.4 g) in two separate portions. After being stirred for 3 hours, the reaction solution was dropped to water (2,000 ml), and the precipitated solid was collected by filtration. Toluene (1,000 ml) was added to dissolve the solid, and the solid was dried over magnesium sulfate. After filtration, the filtrate was concentrated. The resulting concentrate was dispersed and washed by addition of n-hexane (200 ml), and dried overnight under reduced pressure to obtain a reddish solid of (biphenyl-4-yl)-4-bromo(phenyl-2,3,5,6-d$_4$)amine (23.4 g; yield 89.0%).

The resulting (biphenyl-4-yl)-4-bromo(phenyl-2,3,5,6-d$_4$) amine (23.0 g), phenylboronic acid (9.4 g), tripotassium phosphate (59.5 g), and THF (460 ml) were added to a nitrogen-substituted reaction vessel, and aerated with nitrogen gas for 30 min under ultrasonic irradiation. The mixture was heated after adding palladium acetate (0.8 g) and tri(tert-butyl)phosphine (2.1 g), and stirred at 60° C. for 12.5 hours while adding palladium acetate (2.0 g), tri(tert-butyl)phosphine (5.2 g), and phenylboronic acid (1.7 g). After being cooled to room temperature, the mixture was concentrated under reduced pressure with water (100 ml) and toluene (320 ml). After being stirred with addition of toluene (100 ml) and water (300 ml), the organic layer was separated and collected. The organic layer was dried over magnesium sulfate, concentrated, and dispersed and washed using methanol (350 ml). The product was dried overnight under reduced pressure to obtain a white brown solid of (biphenyl-4-yl)-[(biphenyl-2,3,5,6-d$_4$)-4-yl]amine (16.6 g; yield 72.7%).

The resulting (biphenyl-4-yl)-[(biphenyl-2,3,5,6-d$_4$)-4-yl]amine (16.3 g), 4,4'-diiodobiphenyl (8.5 g), a copper powder (0.1 g), potassium carbonate (8.6 g), sodium bisulfite (0.7 g), 3,5-di(tert-butyl)salicylic acid (0.5 g), xylene (35 ml), and dodecylbenzene (20 ml) were added to a nitrogen-substituted reaction vessel. The mixture was heated while removing the xylene by distillation, and stirred at 210° C. for 26.5 hours while adding a copper powder (0.4 g), potassium carbonate (8.7 g), sodium bisulfite (2.0 g), 3,5-di(tert-butyl)salicylic acid (0.52 g), and o-dichlorobenzene (4 ml). After cooling to 100° C., toluene (70 ml) was added. The mixture was further cooled to room temperature, and the precipitated solid was collected by filtration. The solid was dispersed and washed by addition of water (200 ml) and methanol (20 ml), and dissolved by being heated to 100° C. after adding o-dichlorobenzene (3.2 L). After removing the insoluble matter by filtration, the product was concentrated, and recrystallized four times with o-dichlorobenzene. After adding methanol (300 ml), the mixture was stirred for 1 hour under heat and reflux, and allowed to cool to room temperature. The precipitated solid was collected by filtration, and dried overnight under reduced pressure to obtain a pale yellow solid of 4,4'-bis{(biphenyl-4-yl)-[(biphenyl-2,3,5,6-d$_4$)-4-yl]amino}biphenyl (Compound 18; 14.6 g; yield 87.2%).

Figure 3:
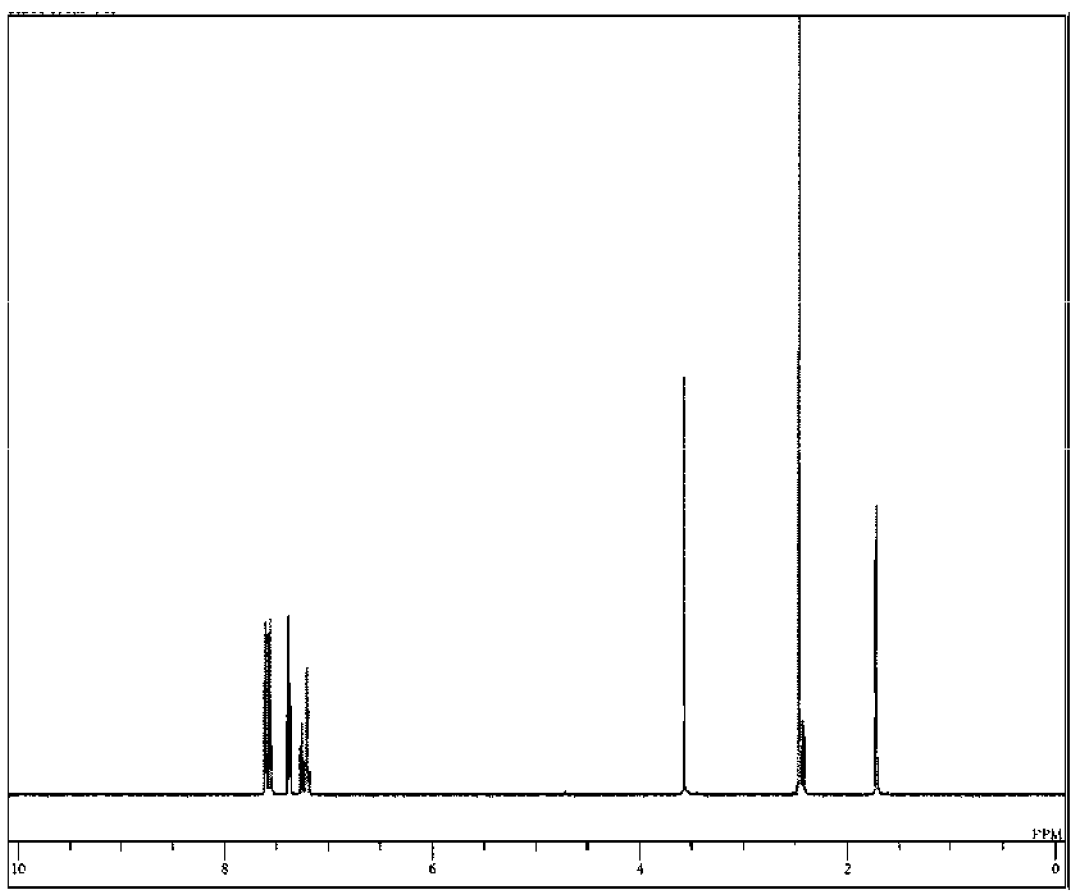
FIG. 3 is a $^1$H-NMR chart of the compound of Example 3 of the present invention (Compound 18).

The structure of the resulting pale yellow solid was identified by NMR. The $^1$H-NMR measurement result is presented in FIG. 3.

1H-NMR (THF-d$_8$) detected 36 hydrogen signals, as follows. δ(ppm)=7.61 (8H), 7.57 (8H), 7.39 (8H), 7.26 (4H), 7.23-7.20 (8H)

Example 4

Synthesis of 4,4'-bis{(biphenyl-4-yl)-[(biphenyl-1',2',3',5',6'-d$_5$)-4-yl]amino}biphenyl (Compound 19)

(Biphenyl-4-yl)-phenylamine (35.0 g) and DMF (700 ml) were added and dissolved in a nitrogen-substituted reaction vessel, and N-bromosuccinimide (8.5 g) was added under ice-cooled conditions. The reaction temperature was raised to room temperature while adding N-bromosuccinimide (17.0 g) in two separate portions. After being stirred for 25.5 hours, the reaction solution was dropped to water (3,500 ml), and the precipitated solid was collected by filtration. Toluene (2,500 ml) was added to dissolve the solid, and the solid was dried over magnesium sulfate. After filtration, the filtrate was concentrated. The resulting concentrate was dispersed and washed by addition of n-hexane (500 ml), and dried overnight under reduced pressure to obtain a reddish solid of (biphenyl-4-yl)-(4-bromophenyl)amine (44.1 g; yield 95.4%).

The resulting (biphenyl-4-yl)-(4-bromophenyl)amine (44.0 g), (phenyl-d$_5$)boronic acid (19.0 g), tripotassium phosphate (115.2 g), and THF (880 ml) were added to a nitrogen-substituted reaction vessel, and aerated with nitrogen gas for 30 min under ultrasonic irradiation. The mixture was heated after adding palladium acetate (1.5 g) and tri(tert-butyl)phosphine (5.5 g), and stirred at 65° C. for 16.5 hours while adding palladium acetate (0.8 g), tri(tert-butyl)phosphine (1.6 g), and ((phenyl-d$_5$)boronic acid (2.0 g). After being cooled to room temperature, the reaction mixture was dropped to a mixed solution of toluene (650 ml) and water (250 ml). The resulting solution was concentrated, and the precipitated solid was collected by filtration. The resulting solid was dissolved in toluene (1.3 L), and concentrated after removing the insoluble matter by filtration. The product was purified by recrystallization using toluene, and dried overnight under reduced pressure to obtain a yellow solid of (biphenyl-4-yl)-[(biphenyl-1',2',3',5',6'-d$_5$)-4-yl]amine (19.7 g; yield 44.5%).

The resulting (biphenyl-4-yl)-[(biphenyl-1',2',3',5',6'-d$_5$)-4-yl]amine (19.5 g) 4,4'-diiodobiphenyl (10.1 g), a copper powder (0.2 g), potassium carbonate (10.3 g), sodium bisulfite (0.8 g), 3,5-di(tert-butyl)salicylic acid (0.6 g), xylene (42 ml), and dodecylbenzene (24 ml) were added to a nitrogen-substituted reaction vessel, and heated while removing the xylene by distillation. The mixture was then stirred at 210° C. for 20 hours while adding a copper powder (0.4 g), potassium carbonate (6.8 g), sodium bisulfite (1.6 g), 3,5-di-(tert-butyl)salicylic acid (1.2 g), and dodecylbenzene (24 ml). After cooling to 100° C., toluene (85 ml) was added. The mixture was further cooled to room temperature, and the precipitated solid was collected by filtration. The solid was dispersed and washed by addition of water (250 ml) and methanol (25 ml), and dissolved by being heated to 100° C. after adding o-dichlorobenzene (4.0 L). The product was concentrated after removing the insoluble matter by filtration, and recrystallized three times using o-dichlorobenzene. After adding methanol (400 ml), the mixture was stirred for 1 hour under heat and reflux, and allowed to cool to room temperature. The precipitated solid was collected by filtration, and dried overnight under reduced pressure to obtain a pale yellow solid of 4,4'-bis{(biphenyl-4-yl)-[(biphenyl-1',2',3',5',6'-d$_5$)-4-yl]amino}biphenyl (Compound 19; 18.2 g; yield 91.0%).

Figure 4:
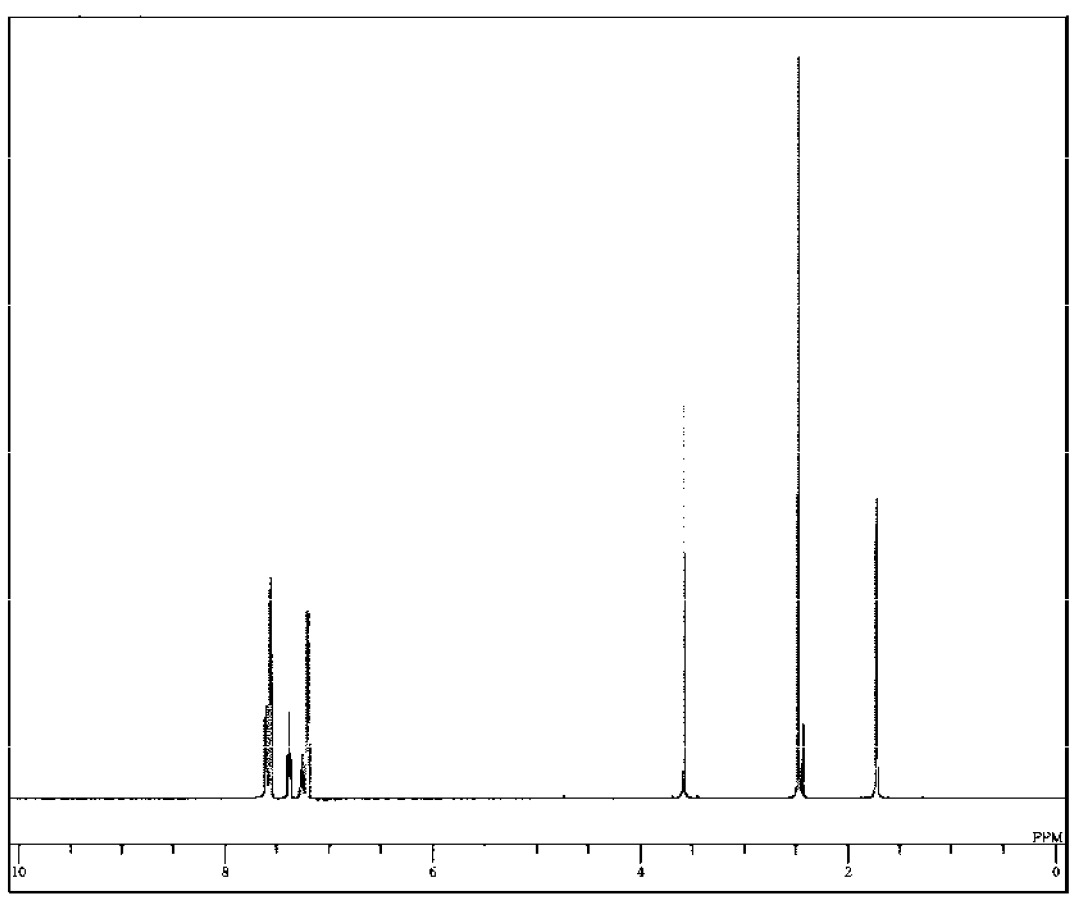
FIG. 4 is a $^1$H-NMR chart of the compound of Example 4 of the present invention (Compound 19).

The structure of the resulting pale yellow solid was identified by NMR. The $^1$H-NMR measurement result is presented in FIG. 4.

Example 5

Synthesis of 4,4'-bis{(bis[(biphenyl-1',2',3',5',6'-$d_5$)-4-yl]amino}biphenyl (Compound 20)

Bis(4-bromophenyl)amine (20.7 g), (phenyl-$d_5$)boronic acid (17.0 g), tripotassium phosphate (53.5 g), and THF (340 ml) were added to a nitrogen-substituted reaction vessel, and aerated with nitrogen gas for 30 min under ultrasonic irradiation. After adding palladium acetate (0.7 g) and tri(tert-butyl) phosphine (1.9 g), the mixture was heated while adding palladium acetate (1.8 g), tri(tert-butyl)phosphine (3.8 g), and tripotassium phosphate (53.5 g), and stirred at 60° C. for 16.5 hours. The mixture was allowed to cool to room temperature, concentrated after removing the insoluble matter by filtration, and recrystallized from toluene to obtain a solid. The solid was dried overnight under reduced pressure to obtain a black yellow solid of bis[(biphenyl-1',2',3',5',6'-$d_5$)-4-yl]amine (8.0 g; yield 37.7%).

The resulting bis[(biphenyl-1',2',3',5',6'-$d_5$)-4-yl]amine (8.00 g), 4,4'-diiodobiphenyl (4.10 g), a copper powder (0.06 g), potassium carbonate (4.20 g), sodium bisulfite (0.32 g), 3,5-di(tert-butyl)salicylic acid (0.25 g), xylene (19 ml), and dodecylbenzene (9 ml) were added to a nitrogen-substituted reaction vessel, heated while removing the xylene by distillation, and stirred at 210° C. for 12 hours. After cooling to 130° C., toluene (35 ml) was added. The mixture was further cooled to room temperature, and the precipitated solid was collected by filtration. The solid was dispersed and washed by addition of water (50 ml) and methanol (10 ml), and dissolved by being heated to 100° C. after adding o-dichlorobenzene (1.4 L). The product was concentrated after removing the insoluble matter by filtration, and recrystallized four times using o-dichlorobenzene. After adding methanol (80 ml), the mixture was stirred for 1 hour under heat and reflux, and allowed to cool to room temperature. The precipitated solid was collected by filtration, and dried overnight under reduced pressure to obtain a pale yellow solid of 4,4'-bis{(bis[(biphenyl-1',2',3',5',6'-$d_5$)-4-yl]amino}biphenyl (Compound 20; 2.7 g; yield 32.9%).

Figure 5:
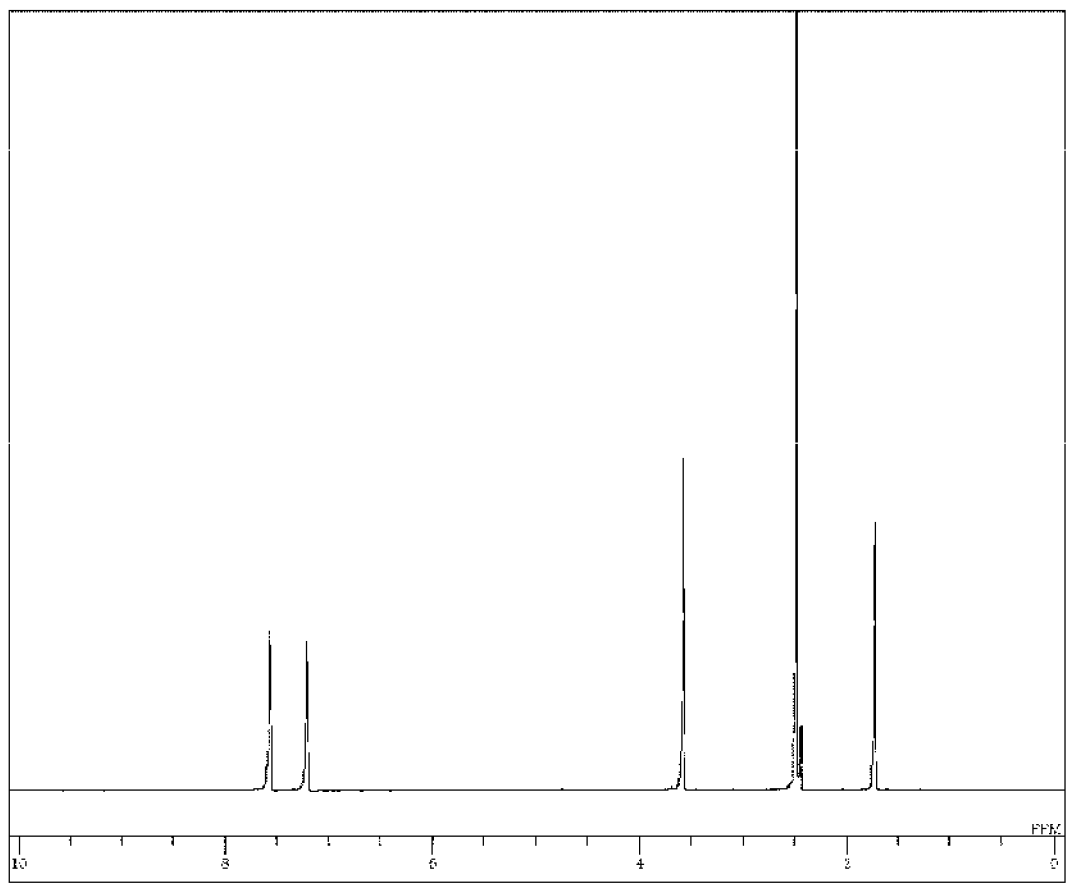
FIG. 5 is a $^1$H-NMR chart of the compound of Example 5 of the present invention (Compound 20).

The structure of the resulting pale yellow solid was identified by NMR. The $^1$H-NMR measurement result is presented in FIG. 5.

1H-NMR (THF-$d_8$) detected 24 hydrogen signals, as follows. δ(ppm)=7.57 (12H), 7.21 (12H).

Example 6

Synthesis of 4,4'-bis[bis(biphenyl-4-yl)amino]biphenyl-2,3,5,6,2',3',5',6'-$d_8$ (Compound 21)

Bis(biphenyl-4-yl)amine (20.0 g), bromobenzene-$d_5$ (10.2 g), tert-butoxy sodium (9.0 g), and toluene (150 ml) were added to a nitrogen-substituted reaction vessel, and aerated with nitrogen gas for 30 min under ultrasonic irradiation. The mixture was heated after adding palladium acetate (0.2 g) and tri(tert-butyl)phosphine (0.5 g), and stirred at 90° C. for 2 hours. After being allowed to cool to room temperature, the reaction mixture was dispersed and washed by addition of methanol (100 ml), and dissolved by addition of toluene (102 ml). The mixture was then concentrated after adsorption purification using a silica gel (20 g). The product was then dispersed and washed by addition of methanol (100 ml), and dried overnight under reduced pressure to obtain a white solid of N-(phenyl-$d_5$)-bis(biphenyl-4-yl)amine (20.1 g; yield 80.1%).

The resulting N-(phenyl-$d_5$)-bis(biphenyl-4-yl)amine (5.00 g), copper perchlorate hexahydrate (6.90 g), toluene (58 ml), and acetonitrile (20 ml) were added to a nitrogen-substituted reaction vessel, and stirred for 57 hours at room temperature. The mixture was dispersed and washed by addition of 3% ammonia water (43 ml), and then with water (200 ml). After adding o-dichlorobenzene (400 ml), the mixture was heated to 100° C. and dissolved. The product was concentrated after removing the insoluble matter by filtration, and recrystallized six times using o-dichlorobenzene. After adding methanol (30 ml) to the resulting crystals, the mixture was stirred for 1 hour under heat and reflux. The mixture was then allowed to cool to room temperature. The solid was collected by filtration, and dried overnight under reduced pressure to obtain a pale yellow solid of 4,4'-bis[bis(biphenyl-4-yl)amino]biphenyl-2,3,5,6,2',3',5',6'-$d_8$ (Compound 21; 2.5 g; yield 50.5%).

Figure 6:
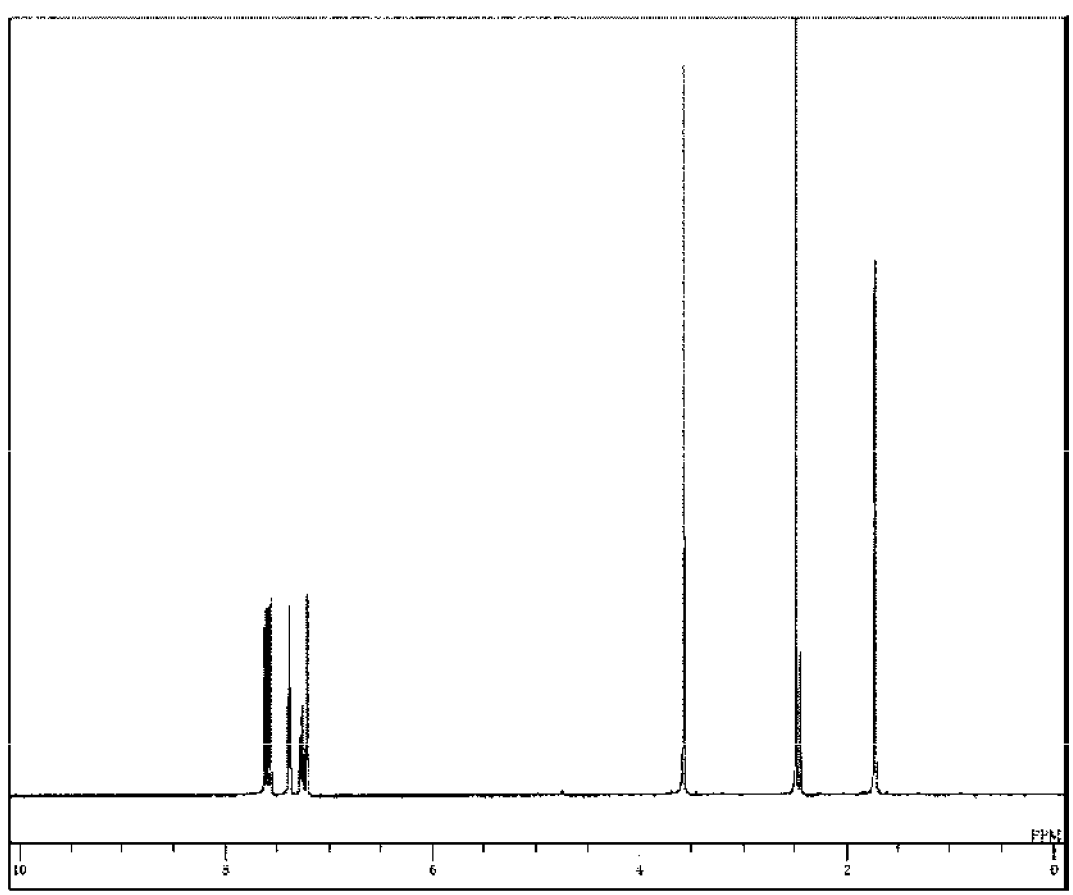
FIG. 6 is a $^1$H-NMR chart of the compound of Example 6 of the present invention (Compound 21).

The structure of the resulting pale yellow solid was identified by NMR. The $^1$H-NMR measurement result is presented in FIG. 6.

1H-NMR (THF-$d_8$) detected 36 hydrogen signals, as follows. δ(ppm)=7.61 (8H), 7.57 (8H), 7.39 (8H), 7.27 (4H), 7.22 (8H)

Example 7

Synthesis of 4,4'-bis{[(4'-diphenylamino)biphenyl-4-yl]-(phenyl-$d_5$)amino}biphenyl (Compound 40)

N-(Phenyl-$d_5$)-benzamide (36.00 g), 4,4'-diiodobiphenyl (144.54 g), a copper powder (2.26 g), potassium carbonate (29.52 g), sodium bisulfite (3.70 g), xylene (180 ml), and dodecylbenzene (90 ml) were added to a nitrogen-substituted reaction vessel, and heated while removing the xylene (150 ml) by distillation. The mixture was stirred at 200° C. for 16.5 hours while adding a copper powder (2.26 g) and potassium carbonate (4.92 g) in two separate portions. After being cooled to 80° C., toluene (1,000 ml) was added. After further cooling to 50° C., the insoluble matter was removed by filtration. The product was concentrated, and purified by adsorption using a silica gel after adding hexane (800 ml). The product was further concentrated after adsorption purification using a NH silica gel to obtain a while powder of N-[(4'-iodo)biphenyl-4-yl]-N-(phenyl-$d_5$)-benzamide (35.58 g; yield 41%).

The resulting N-[(4'-iodo)biphenyl-4-yl]-N-(phenyl-$d_5$)-benzamide (33.43 g), diphenylamine (14.13 g), a copper powder (0.45 g), potassium carbonate (14.43 g), sodium bisulfite (1.08 g), and dodecylbenzene (56 ml) were added to a nitrogen-substituted reaction vessel, heated, and stirred at 210° C. for 7.5 hours while adding a copper powder (0.45 g) and potassium carbonate (0.96 g). After cooling to 80° C., toluene (500 ml) was added. The mixture was further cooled to 60° C., and the insoluble matter was removed by filtration. The product was concentrated, and added to a different reaction vessel. After adding potassium hydroxide (9.76 g), water (11 ml), and isoamyl alcohol (49 ml), the mixture was stirred for 3 hours while being heated. The mixture was allowed to cool to room temperature, stirred after adding toluene (500 ml) and water (500 ml), and separated to collect the organic layer. The organic layer was dried over magnesium sulfate, and concentrated under reduced pressure. After adding hexane (400 ml), the precipitated solid was collected by filtration to obtain a crude product. The crude product was purified by column chromatography (carrier: silica gel; eluent: cyclohexane/toluene) to obtain a white powder of 4'-diphenylamino-4-[(phenyl-$d_5$)amino]biphenyl (16.38 g; yield 56%).

The resulting 4'-diphenylamino-4-[(phenyl-$d_5$)amino]biphenyl (16.00 g), 4,4'-diiodobiphenyl (7.1 g), a copper powder (0.11 g), potassium carbonate (3.61 g), sodium bisulfite (0.27 g) xylene (19 ml), and dodecylbenzene (11 ml) were added to a nitrogen-substituted reaction vessel, and heated while removing the xylene (12 ml) by distillation. The mixture was stirred at 210° C. for 10 hours while adding a copper powder (0.11 g) and potassium carbonate (0.24 g). After cooling to 80° C., toluene (250 ml) was added. The mixture was further cooled to 60° C., and the insoluble matter was removed by filtration. The mixture was concentrated, and purified by being recrystallized four times using a toluene/ethyl acetate mixed solvent to obtain a pale yellowish white powder of 4,4'-bis{[(4'-diphenylamino)biphenyl-4-yl]-(phenyl-$d_5$)amino}biphenyl (Compound 40; 14.01 g; yield 82%).

Figure 7:
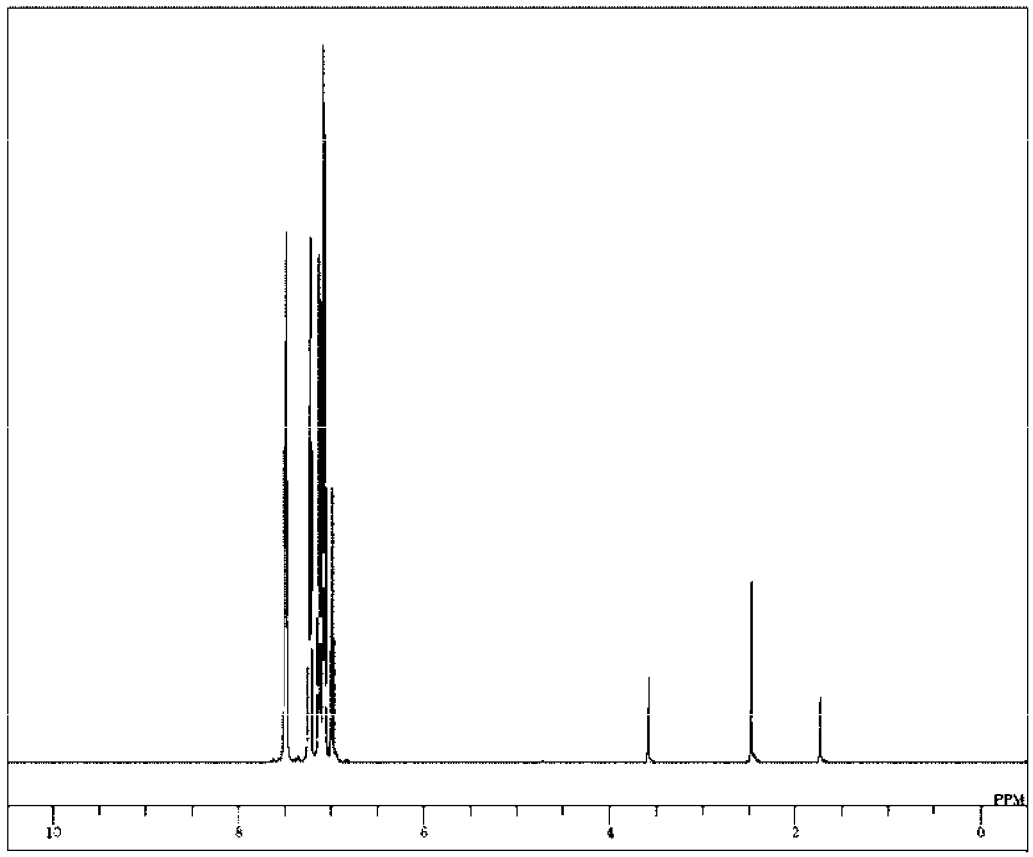
FIG. 7 is a $^1$H-NMR chart of the compound of Example 7 of the present invention (Compound 40).

The structure of the resulting pale yellowish white powder was identified by NMR. The $^1$H-NMR measurement result is presented in FIG. 7.

1H-NMR (THF-$d_8$) detected 44 hydrogen signals, as follows. δ(ppm)=6.99 (4H), 7.06-7.16 (20H), 7.23 (8H), 7.47-7.54 (12H)

Example 8

The glass transition points of the compounds of the present invention, and the glass transition points of the comparative compounds 50, 51, and 52 corresponding to the compounds of the present invention but unsubstituted with deuterium atoms were determined using a high-sensitive differential scanning calorimeter DSC 3100S produced by Bruker AXS.

|  | Glass transition point |
|---|---|
| Compound of Example 1 of the present invention | 100° C. |
| Compound of Example 2 of the present invention | 101° C. |
| Comparative compound 50 | 101° C. |
| Compound of Example 3 of the present invention | 134° C. |
| Compound of Example 4 of the present invention | 133° C. |
| Compound of Example 5 of the present invention | 134° C. |
| Compound of Example 6 of the present invention | 133° C. |
| Comparative compound 51 | 132° C. |
| Compound of Example 7 of the present invention | 144° C. |
| Comparative compound 52 | 144° C. |

[Chemical Formula 65]

(Comparative Compound 50)

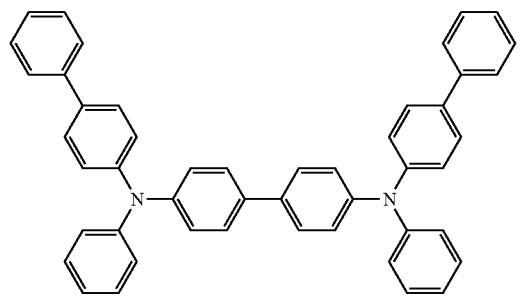

[Chemical Formula 66]

(Comparative Compound 51)

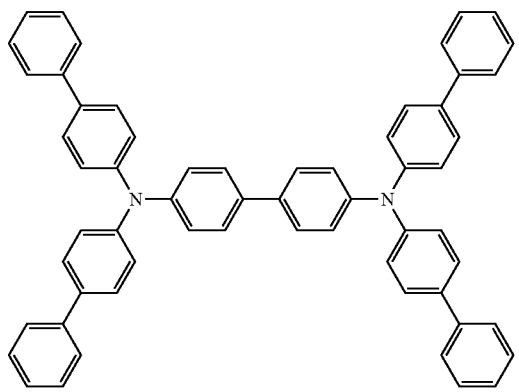

[Chemical Formula 67]

(Comparative Compound 52)

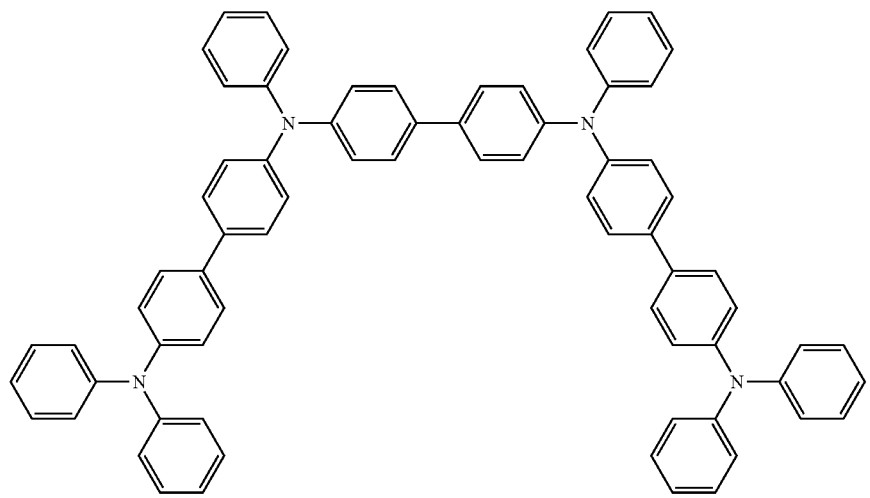

The compounds of the present invention have glass transition points of 90° C. or higher, demonstrating that the compounds of the present invention have a stable thin-film state. Further, the compounds of Examples 1 and 2 of the present invention have nearly the same glass transition points as the corresponding comparative compound 50 unsubstituted with a deuterium atom. Further, the compounds of Examples 3 to 6 of the present invention have nearly the same glass transition points as the corresponding comparative compound 51 unsubstituted with a deuterium atom. The compound of Example 7 of the present invention has nearly the same glass transition point as the corresponding comparative compound 52 unsubstituted with a deuterium atom.

Example 9

A 100 nm-thick vapor-deposited film was fabricated on an ITO substrate using the compounds of the present invention, and the work function was measured using an atmosphere photoelectron spectrometer (Model AC-2 produced by Riken Keiki Co., Ltd.).

|  | Work function |
|---|---|
| Compound of Example 1 of the present invention | 5.47 eV |
| Compound of Example 2 of the present invention | 5.51 eV |
| Comparative compound 50 | 5.46 eV |
| Compound of Example 3 of the present invention | 5.43 eV |
| Compound of Example 4 of the present invention | 5.44 eV |
| Compound of Example 5 of the present invention | 5.43 eV |
| Compound of Example 6 of the present invention | 5.42 eV |
| Comparative compound 51 | 5.45 eV |
| Compound of Example 7 of the present invention | 5.43 eV |
| Comparative compound 52 | 5.44 eV |

As the results show, the compounds of the present invention have desirable energy levels compared to the work function 5.4 eV of common hole transport materials such as NPD and TPD, and thus possess desirable hole transportability. Further, the compounds of Examples 1 and 2 of the present invention have nearly the same energy levels as the corresponding comparative compound 50 unsubstituted with a deuterium atom. Further, the compounds of Examples 3 to 6 of the present invention have nearly the same energy levels as the corresponding comparative compound 51 unsubstituted with a deuterium atom. The compound of Example 7 of the present invention has nearly the same energy level as the corresponding comparative compound 52 unsubstituted with a deuterium atom.

Example 10

Figure 8:
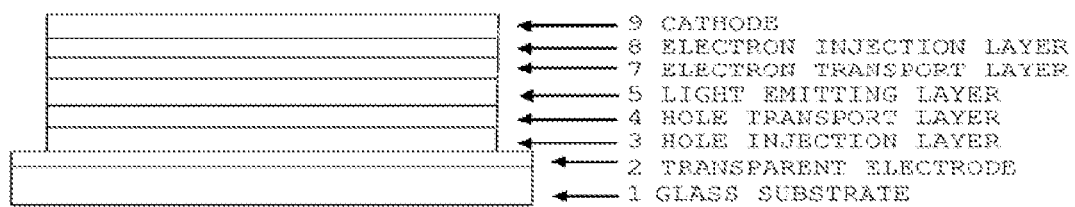
FIG. 8 is a diagram representing the configuration of the EL devices of Example 10 and Comparative Example 1.

The organic EL device, as illustrated in FIG. 8, was fabricated from a hole injection layer 3, a hole transport layer 4, a light emitting layer 5, an electron transport layer 7, an electron injection layer 8, and a cathode (aluminum electrode) 9 successively formed by vapor deposition on a glass substrate 1 that had been provided beforehand with an ITO electrode as a transparent anode 2.

Specifically, the glass substrate 1 having ITO (thickness 150 nm) formed thereon was washed with an organic solvent, and subjected to an oxygen plasma treatment to wash the surface. The glass substrate with the ITO electrode was then installed in a vacuum vapor deposition apparatus, and the pressure was reduced to 0.001 Pa or less. This was followed by formation of the hole injection layer 3 by forming the compound 52 of the structural formula above over the transparent anode 2 in a thickness of 20 nm. The hole transport layer 4 was then formed on the hole injection layer 3 by forming the compound of Example 1 of the present invention (compound 5) in a thickness of 40 nm. Thereafter, the light emitting layer 5 was formed on the hole transport layer 4 by forming the compounds 53 and 54 of the structural formulae below in a thickness of 30 nm using dual vapor deposition at a deposition rate ratio of compound 53:compound 54=5:95. Then, the electron transport layer 7 was formed on the light emitting layer 5 by forming $Alq_3$ in a thickness of 30 nm. The electron injection layer 8 was then formed on the electron transport layer 7 by forming lithium fluoride in a thickness of 0.5 nm. Finally, the cathode 9 was formed by vapor depositing aluminum in a thickness of 150 nm. The characteristics of the organic EL device thus fabricated were measured in an atmosphere at ordinary temperature.

Table 1 summarizes the results of the emission characteristics measurements performed by applying a DC voltage to the organic EL device produced by using the compound of Example 1 of the present invention (compound 5).

[Chemical Formula 68]

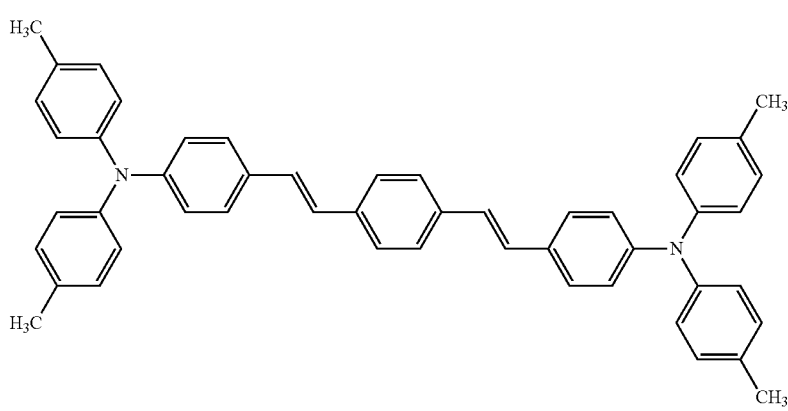

(Compound 53)

[Chemical Formula 69]

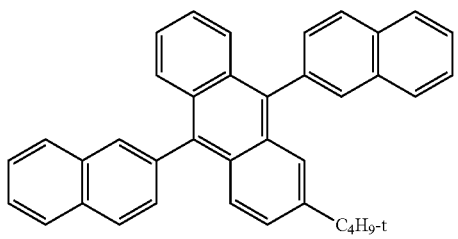

Comparative Example 1

For comparison, an organic EL device was fabricated under the same conditions used in Example 10, except that the comparative compound 50 was formed in a thickness of nm as the material of the hole transport layer 4, instead of using the compound of Example 1 of the present invention (compound 5). The characteristics of the organic EL device thus fabricated were measured in an atmosphere at ordinary temperature. Table 1 summarizes the results of the emission characteristics measurements performed by applying a DC voltage to the organic EL device.

TABLE 1

| | Compound | Voltage [V] (@ 10 mA/cm$^2$) | Current efficiency [cd/A] (@ 10 mA/cm$^2$) | Power efficiency [lm/W] (@ 10 mA/cm$^2$) |
|---|---|---|---|---|
| Example 10 | Compound 5 | 5.02 | 9.00 | 5.60 |
| Comparative Example 1 | Comparative compound 50 | 4.97 | 8.53 | 5.40 |

As can be seen in Table 1, the driving voltage upon passing a current with a current density of 10 mA/cm$^2$ was 5.02 V for the compound of Example 1 of the present invention (compound 5), about the same as the driving voltage 4.97 V for the comparative compound 50. Further, the compound of Example 1 of the present invention (compound 5) had a current efficiency of 9.00 cd/A, a great improvement over the current efficiency 8.53 cd/A of the comparative compound 50. The power efficiency also improved from the 5.40 μm/W of the comparative compound 50 to 5.60 μm/W in the compound of Example 1 of the present invention (compound 5).

As these results clearly demonstrate, the organic EL device using the arylamine compound having a triphenylamine structure according to the present invention can have improved luminous efficiency and power efficiency compared to the known organic EL device using the comparative compound 50 unsubstituted with a deuterium atom.

The results of turn on voltage measurements using the foregoing organic EL devices are presented below.

| Organic EL device | Compound | Turn on voltage [V] |
|---|---|---|
| Example 10 | Compound 5 | 2.7 |
| Comparative Example 1 | Comparative compound 50 | 2.8 |

It can be seen from these results that the turn on voltage is nearly the same between Comparative Example 1 in which the comparative compound 50 unsubstituted with a deuterium atom was used, and Example 10 in which the compound of Example 1 of the present invention (compound 5) was used.

Example 11

Figure 9:
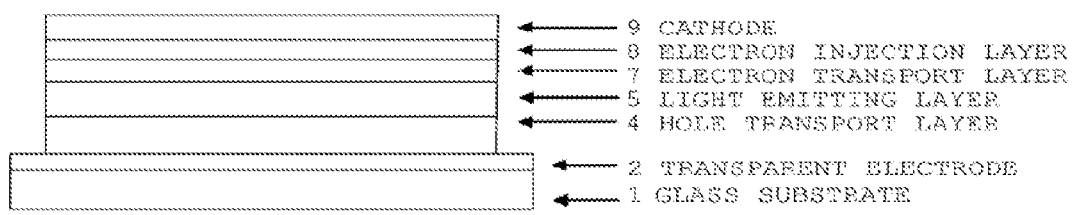
FIG. 9 is a diagram representing the configuration of the EL devices of Examples 11 to 14 and Comparative Example 2.

The organic EL device, as illustrated in FIG. 9, was fabricated from a hole transport layer 4, a light emitting layer 5, an electron transport layer 7, an electron injection layer 8, and a cathode (aluminum electrode) 9 successively formed by vapor deposition on a glass substrate 1 that had been provided beforehand with an ITO electrode as a transparent anode 2.

Specifically, the glass substrate 1 having ITO (thickness 150 nm) formed thereon was washed with an organic solvent, and subjected to an oxygen plasma treatment to wash the surface. The glass substrate with the ITO electrode was then installed in a vacuum vapor deposition apparatus, and the pressure was reduced to 0.001 Pa or less. This was followed by formation of the hole transport layer 4 by forming the compound of Example of the present invention (compound 5) over the transparent electrode 2 in a thickness of 60 nm. The light emitting layer 5 was then formed on the hole transport layer 4 by forming the compounds 53 and 54 in a thickness of 30 nm using dual vapor deposition at a deposition rate ratio of compound 53:compound 54=5:95. Then, the electron transport layer 7 was formed on the light emitting layer 5 by forming the compound 55 of the structural formula below in a thickness of 30 nm. The electron injection layer 8 was then formed on the electron transport layer 7 by forming lithium fluoride in a thickness of 0.5 nm. Finally, the cathode 9 was formed by vapor depositing aluminum in a thickness of 150 nm. The characteristics of the organic EL device thus fabricated were measured in an atmosphere at ordinary temperature.

[Chemical Formula 70]

(Compound 55)

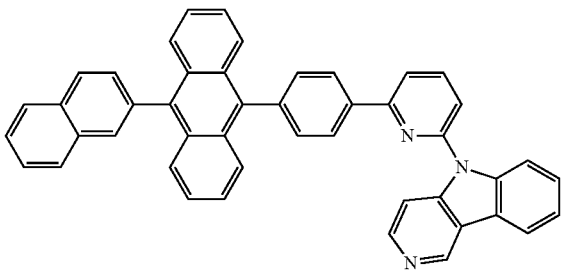

Table 2 summarizes the results of the emission characteristics measurements performed by applying a DC voltage to the organic EL device produced by using the compound of Example 1 of the present invention (compound 5).

Example 12

An organic EL device was fabricated under the same conditions used in Example 11, except that the compound of Example 4 of the present invention (compound 19) was formed in a thickness of 60 nm as the material of the hole transport layer 4, instead of using the compound of Example 1 of the present invention (compound 5). The characteristics of the organic EL device thus fabricated were measured in an atmosphere at ordinary temperature. Table 2 summarizes the results of the emission characteristics measurements performed by applying a DC voltage to the organic EL device.

Example 13

An organic EL device was fabricated under the same conditions used in Example 11, except that the compound of Example 6 of the present invention (compound 21) was formed in a thickness of 60 nm as the material of the hole transport layer 4, instead of using the compound of Example 1 of the present invention (compound 5). The characteristics of the organic EL device thus fabricated were measured in an atmosphere at ordinary temperature. Table 2 summarizes the results of the emission characteristics measurements performed by applying a DC voltage to the organic EL device.

Example 14

An organic EL device was fabricated under the same conditions used in Example 11, except that the compound of Example 7 of the present invention (compound 40) was formed in a thickness of 60 nm as the material of the hole transport layer 4, instead of using the compound of Example 1 of the present invention (compound 5). The characteristics of the organic EL device thus fabricated were measured in an atmosphere at ordinary temperature. Table 2 summarizes the results of the emission characteristics measurements performed by applying a DC voltage to the organic EL device.

Comparative Example 2

For comparison, an organic EL device was fabricated under the same conditions used in Example 11, except that the comparative compound 50 was formed in a thickness of nm as the material of the hole transport layer 4, instead of using the compound of Example 1 of the present invention (compound 5). The characteristics of the organic EL device thus fabricated were measured in an atmosphere at ordinary temperature. Table 2 summarizes the results of the emission characteristics measurements performed by applying a DC voltage to the organic EL device.

TABLE 2

| | Compound | Voltage [V] (@ 10 mA/cm$^2$) | Current efficiency [cd/A] (@ 10 mA/cm$^2$) | Power efficiency [lm/W] (@ 10 mA/cm$^2$) |
|---|---|---|---|---|
| Example 11 | Compound 5 | 4.02 | 8.82 | 6.89 |
| Example 12 | Compound 19 | 4.24 | 10.50 | 7.78 |
| Example 13 | Compound 21 | 4.18 | 10.83 | 8.14 |
| Example 14 | Compound 40 | 3.96 | 9.62 | 7.63 |
| Comparative Example 2 | Comparative compound 50 | 4.01 | 8.80 | 6.90 |

As can be seen from Table 2, the organic EL devices using the compounds of Examples of the present invention have the driving voltage, current efficiency, and power efficiency comparable to or better than those of the organic EL device using the comparative compound 50, as measured upon passing a current with a current density of 10 mA/cm$^2$.

Table 3 summarizes the results of the device life measurements performed with organic EL devices fabricated in the manner described in Example 11 and Comparative Example 2. Device life was measured as the time where the emission luminance of 350 cd/m$^2$ under a constant current amount (W) attenuated to 97 from the initial luminance 100.

TABLE 3

| | Compound | Device life |
|---|---|---|
| Example 11 | Compound 5 | 83 h |
| Comparative Example 2 | Comparative compound 50 | 8 h |

As can be seen from Table 3, the organic EL device using the compound of Example 1 of the present invention (compound 5) has a much longer device life than the organic EL device using the comparative compound 50 unsubstituted with a deuterium atom.

Table 4 summarizes the results of the device life measurements performed with organic EL devices fabricated in the manner described in Examples 11 to 14 and Comparative Example 2. Device life was measured as the time where the emission luminance of 5,000 cd/m$^2$ under a constant current amount (W) attenuated to 50 from the initial luminance 100 (luminance half-life).

TABLE 4

| | Compound | Half-life (hours) |
|---|---|---|
| Example 11 | Compound 5 | 835 |
| Example 12 | Compound 19 | 859 |
| Example 13 | Compound 21 | 868 |
| Example 14 | Compound 40 | 830 |
| Comparative Example 2 | Comparative compound 50 | 360 |

As can be seen from Table 4, the organic EL devices using the compounds of Examples of the present invention have much longer device lives than the organic EL device using the comparative compound 50 unsubstituted with a deuterium atom.

Example 15

Figure 10:
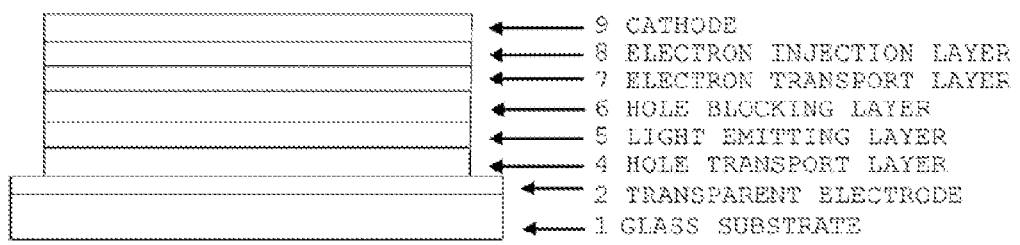
FIG. 10 is a diagram representing the configuration of the EL devices of Examples 15 to 18 and Comparative Example 3.

The organic EL device, as illustrated in FIG. 10, was fabricated from a hole transport layer 4, a light emitting layer 5, a hole blocking layer 6, an electron transport layer 7, an electron injection layer 8, and a cathode (aluminum electrode) 9 successively formed by vapor deposition on a glass substrate 1 that had been provided beforehand with an ITO electrode as a transparent anode 2.

Specifically, the glass substrate 1 having ITO (thickness 150 nm) formed thereon was washed with an organic solvent, and subjected to an oxygen plasma treatment to wash the surface. The glass substrate with the ITO electrode was then installed in a vacuum vapor deposition apparatus, and the pressure was reduced to 0.001 Pa or less. This was followed by formation of the hole transport layer 4 by forming the compound of Example of the present invention (compound 5) over the transparent anode 2 in a thickness of 50 nm. The light emitting layer 5 was then formed on the hole transport layer 4 by forming TPBI and Ir(ppy)$_3$ in a thickness of 20 nm using dual vapor deposition at a deposition rate ratio of TPBI:Ir(ppy)$_3$=92:8. Then, the hole blocking layer 6 was formed on the light emitting layer 5 by forming BCP in a thickness of 10 nm. The electron transport layer 7 was then formed on the hole blocking layer 6 by forming Alq₃ in a thickness of 30 nm. Then, the electron injection layer 8 was formed on the electron transport layer 7 by forming lithium fluoride in a thickness of 0.5 nm. Finally, the cathode 9 was formed by vapor depositing aluminum in a thickness of 150 nm. The characteristics of the organic EL device thus fabricated were measured in an atmosphere at ordinary temperature. Table 5 summarizes the results of the emission characteristics measurements performed by applying a DC voltage to the organic EL device.

Example 16

An organic EL device was fabricated under the same conditions used in Example 15, except that the compound of Example 4 of the present invention (compound 19) was formed in a thickness of 50 nm as the material of the hole transport layer 4, instead of using the compound of Example 1 of the present invention (compound 5). The characteristics of the organic EL device thus fabricated were measured in an atmosphere at ordinary temperature. Table 0.5 summarizes the results of the emission characteristics measurements performed by applying a DC voltage to the organic EL device.

Example 17

An organic EL device was fabricated under the same conditions used in Example 15, except that the compound of Example 6 of the present invention (compound 21) was formed in a thickness of 50 nm as the material of the hole transport layer 4, instead of using the compound of Example 1 of the present invention (compound 5). The characteristics of the organic EL device thus fabricated were measured in an atmosphere at ordinary temperature. Table 5 summarizes the results of the emission characteristics measurements performed by applying a DC voltage to the organic EL device.

Example 18

An organic EL device was fabricated under the same conditions used in Example 15, except that the compound of Example 7 of the present invention (compound 40) was formed in a thickness of 50 nm as the material of the hole transport layer 4, instead of using the compound of Example 1 of the present invention (compound 5). The characteristics of the organic EL device thus fabricated were measured in an atmosphere at ordinary temperature. Table 5 summarizes the results of the emission characteristics measurements performed by applying a DC voltage to the organic EL device.

Comparative Example 3

For comparison, an organic EL device was fabricated under the same conditions used in Example 15, except that the comparative compound 50 was formed in a thickness of nm as the material of the hole transport layer 4, instead of using the compound of Example 1 of the present invention (compound 5). The characteristics of the organic EL device thus fabricated were measured in an atmosphere at ordinary temperature. Table 5 summarizes the results of the emission characteristics measurements performed by applying a DC voltage to the organic EL device.

TABLE 5

| | Compound | Voltage [V] (@ 10 mA/cm²) | Current efficiency [cd/A] (@ 10 mA/cm²) | Power efficiency [lm/W] (@ 10 mA/cm²) |
|---|---|---|---|---|
| Example 15 | Compound 5 | 5.62 | 20.01 | 11.18 |
| Example 16 | Compound 19 | 5.83 | 20.48 | 11.03 |
| Example 17 | Compound 21 | 5.81 | 22.07 | 11.93 |
| Example 18 | Compound 40 | 5.67 | 20.13 | 11.15 |
| Comparative Example 3 | Comparative compound 50 | 5.65 | 19.33 | 10.74 |

As can be seen from Table 5, the organic EL devices using the compounds of Examples of the present invention have the driving voltage, current efficiency, and power efficiency comparable to or better than those of the organic EL device using the comparative compound 50, as measured upon passing a current with a current density of 10 mA/cm².

As the foregoing results clearly demonstrate, the organic EL devices using the compounds of Examples of the present invention have the driving voltage, luminous efficiency, and power efficiency comparable to or better than those of the organic EL device using the comparative compound 50 unsubstituted with a deuterium atom, as measured upon passing a current with a current density of 10 mA/cm².

As is clear from the foregoing results, device performance such as driving voltage, luminous efficiency, and power efficiency are expected to improve in the organic EL device using the arylamine compound having a triphenylamine structure according to the present invention, compared with the known organic EL device using the comparative compound 50 unsubstituted with a deuterium atom. It was also found that the device life could be greatly improved.

INDUSTRIAL APPLICABILITY

The arylamine compound having a triphenylamine structure according to the present invention has high hole-injecting/transporting performance with an electron blocking ability and a stable thin-film state. The arylamine compound therefore has excellent properties for use in an organic EL device. The organic EL device fabricated by using the compound can have high luminous efficiency and power efficiency, and a greatly improved device life. There are potential applications for, for example, home electronic appliances and illuminations.

DESCRIPTION OF REFERENCE NUMERALS AND SIGNS

1 Glass substrate
2 Transparent anode
3 Hole injection layer
4 Hole transport layer
5 Light emitting layer
6 Hole blocking layer
7 Electron transport layer
8 Electron injection layer
9 Cathode

The invention claimed is:
1. The organic electroluminescent device that comprises a pair of electrodes, and a plurality of organic layers sandwiched between the pair of electrodes,
the organic electroluminescent device further including a
light emitting layer that contains a phosphorescent light-emitting material and is sandwiched between the pair of electrodes, wherein the arylamine compound of the general formula (2) is used as a constituent material of at least one organic layer, wherein the arylamine compound of general formula (2) is an arylamine compound having four triphenylamine structures within the molecule, the four triphenylamine structures being connected by a single bond, or by a divalent group that does not contain a heteroatom,

[Chemical Formula 7]

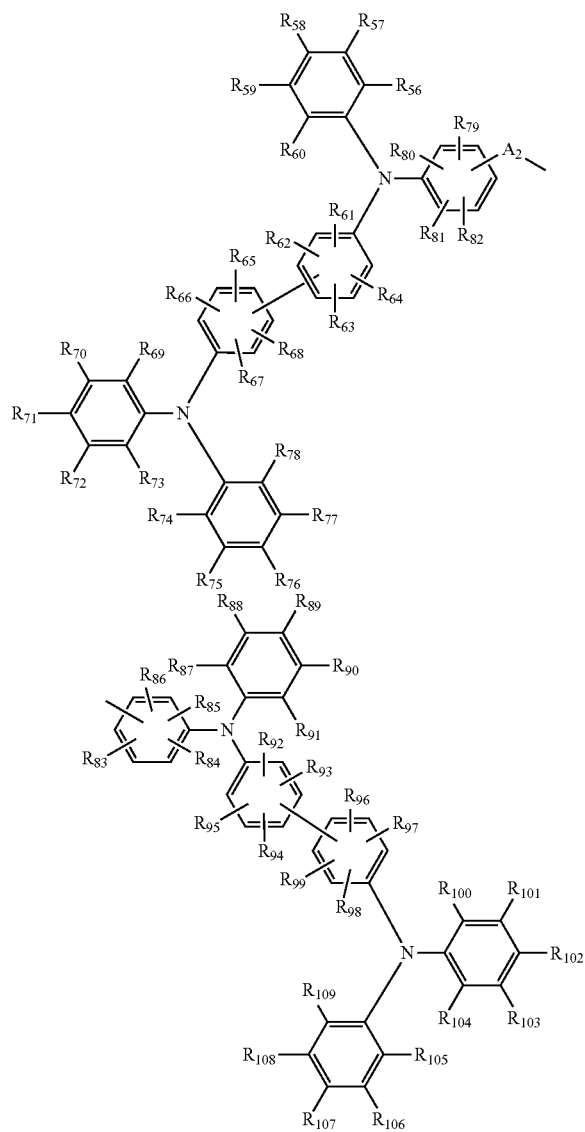

(2)

wherein R56 to R109 may be the same or different, and represent a hydrogen atom, a deuterium atom, a fluorine atom, a chlorine atom, cyano, trifluoromethyl, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, which may bind to each other to form a ring, where at least one of R56 to R109 is a deuterium atom, or a substituent that contains a deuterium atom, and wherein A2 represents the divalent group of the following structural formulae (B) to (F),

[Chemical Formula 8]

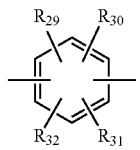

(B)

wherein R29 to R32 may be the same or different, and represent a hydrogen atom or a deuterium atom,

[Chemical Formula 9]

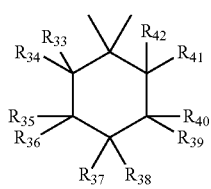

(C)

wherein R33 to R42 may be the same or different, and represent a hydrogen atom or a deuterium atom,

[Chemical Formula 10]

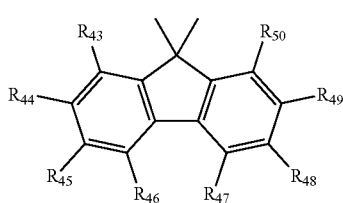

(D)

wherein R43 to R50 may be the same or different, and represent a hydrogen atom or a deuterium atom,

[Chemical Formula 11]

—CH$_2$—     (E)

[Chemical Formula 12]

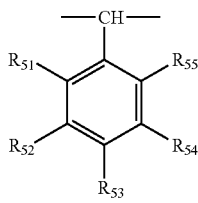

(F)

wherein R51 to R55 may be the same or different, and represent a hydrogen atom or a deuterium atom.

2. The organic electroluminescent device according to claim 1, wherein the organic layer is a hole injection layer.

3. The organic electroluminescent device of claim 1, wherein the organic layer is an electron blocking layer.

4. The organic electroluminescent device of claim 1, wherein the phosphorescent light-emitting material is a metal complex that contains iridium or platinum.

* * * * *